(12) United States Patent
McBride et al.

(10) Patent No.: US 7,238,340 B1
(45) Date of Patent: Jul. 3, 2007

(54) MONOAMINE, DIAMIDE, THIOL-CONTAINING METAL CHELATING AGENTS

(75) Inventors: William McBride, Manchester, NH (US); Richard T. Dean, Bedford, NH (US)

(73) Assignee: CIS bio international, Gif-sur-Yvette (FR)

( * ) Notice: Subject to any disclaimer, the term of this patent is extended or adjusted under 35 U.S.C. 154(b) by 0 days.

(21) Appl. No.: 08/253,973

(22) Filed: Jun. 3, 1994

Related U.S. Application Data

(63) Continuation-in-part of application No. 07/807,062, filed on Nov. 27, 1991, now Pat. No. 5,443,815.

(51) Int. Cl.
*A61K 51/00* (2006.01)
*A61K 49/00* (2006.01)

(52) U.S. Cl. ............ 424/1.69; 424/1.65; 558/254
(58) Field of Classification Search ............... 424/1.65, 424/1.69, 9.341, 1.49; 530/300; 558/254
See application file for complete search history.

(56) References Cited

U.S. PATENT DOCUMENTS

| | | | |
|---|---|---|---|
| 4,434,151 A | 2/1984 | Byrne et al. | |
| 4,444,690 A | 4/1984 | Fritzberg | |
| 4,472,509 A | 9/1984 | Gansow et al. | |
| 4,571,430 A | 2/1986 | Byrne et al. | |
| 4,575,556 A | 3/1986 | Byrne et al. | |
| 4,668,503 A | 5/1987 | Hnatowich | |
| 4,732,864 A | 3/1988 | Tolman | |
| 4,832,940 A | 5/1989 | Ege et al. | |
| 4,861,869 A | 8/1989 | Nicolotti et al. | |
| 4,925,650 A | 5/1990 | Nosco et al. | |
| 4,943,523 A | 7/1990 | Stavrianopoulos | |
| 4,965,392 A | 10/1990 | Fritzberg et al. | |
| 4,986,979 A | 1/1991 | Morgan et al. | |
| 5,061,641 A | 10/1991 | Schochat et al. | |
| 5,091,514 A | 2/1992 | Fritzberg et al. | |
| 5,095,111 A | 3/1992 | Lever et al. | |
| 5,112,953 A | 5/1992 | Gustavson et al. | |
| 5,175,257 A | 12/1992 | Kasina et al. | |
| 5,180,816 A | 1/1993 | Dean et al. | |
| 5,196,515 A | 3/1993 | Lever et al. | |
| 5,248,764 A | 9/1993 | Flanagan et al. | |
| 5,443,816 A * | 8/1995 | Zamora et al. | 424/1.69 |
| 5,662,885 A | 9/1997 | Pollak et al. | 424/1.69 |
| 5,688,485 A * | 11/1997 | Harris | 424/1.65 |
| 5,780,006 A | 7/1998 | Pollak et al. | 424/1.69 |

FOREIGN PATENT DOCUMENTS

| | | |
|---|---|---|
| EP | 84109831.2 | 5/1985 |
| EP | 85104959.3 | 12/1985 |
| EP | 86105920.2 | 11/1986 |
| EP | 87300426.1 | 9/1987 |
| EP | 87118142.6 | 6/1988 |
| EP | 88102252.9 | 8/1988 |
| EP | 88104755.9 | 9/1988 |
| EP | 8802276 | 1/1989 |
| EP | 90306427.5 | 12/1990 |
| EP | 90402206.8 | 2/1991 |
| EP | WO9101144 | 2/1991 |
| EP | 483704 A1 | 5/1992 |
| GB | 8927255.3 | 6/1990 |
| WO | WO8503231 | 8/1985 |
| WO | WO8807382 | 10/1988 |
| WO | WO8907456 | 8/1989 |
| WO | WO8909405 | 10/1989 |
| WO | 8901854 | 11/1989 |
| WO | WO8912625 | 12/1989 |
| WO | WO9006323 | 6/1990 |
| WO | WO9015818 | 12/1990 |
| WO | WO9109876 | 7/1991 |
| WO | 9103116 | 11/1991 |
| WO | 9204559 | 12/1992 |
| WO | WO9312819 | 7/1993 |
| WO | WO9315770 | 8/1993 |

(Continued)

OTHER PUBLICATIONS

Rhodes, 1974, "Considerations in the Radiolabeling of Albumin", *Sem. Nucl. Med.* 4: 281-293.

(Continued)

*Primary Examiner*—Michael G. Hartley
(74) *Attorney, Agent, or Firm*—Fish & Richardson PC

(57) ABSTRACT

Therapeutically active thiazole derivatives of formula (I) wherein $R^1$-$R^2$, X and X' as are defined in the specification, processes for the preparation thereof, the use thereof in therapy, particularly in the treatment or prophylaxis of disorders characterised by overexpression of transforming growth factor • (TGF-•), and pharmaceutical compositions for use in such therapy.

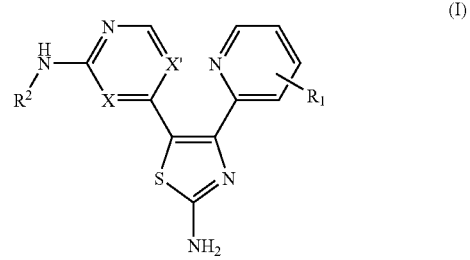

5 Claims, No Drawings

FOREIGN PATENT DOCUMENTS

WO          WO9321151          10/1993

OTHER PUBLICATIONS

Davidson et al., 1981, "A New Class of Oxotechnetium(5+) Chelate Complexes containing a $TcON_2S_2$ Core", Inorg. Chem. 20: 1629-1632.

Fritzberg et al., 1982, "Synthesis and Biological Evaluation of Tc-99m N,N'-Bis(mercaptoacetyl)-2,3-diaminopropanoate: A Potential Replacement for [$^{131}$I]o-iodohippurate", J. Nucl. Med. 23: 592-598.

Khaw et al., 1982, "Technetium-99m Labeling of Antibodies to Cardiac Myosin Fab and to Human Fibrinogen", J. Nucl. Med. 23: 1011-1019.

Byrne and Tolman, 1983, "Technetium-99m Bifunctional Chelating Agent—Thiolactone for Coupling to Biomolecules, $N_2S_2$ Ligand for Chelation to Technetium", J. Nucl. Med. 24: P126.

Bryson et al., 1988, "Neutral Technetium(V) Complexes with Amide-Thiol-Thioether Chelating Ligands", Inorg. Chem. 27: 2154-2161.

Misra et al., 1989, "Synthesis of a Novel Diaminodithiol Ligand for Labeling Proteins and Small Molecules with Technetium-99m", Tet. Lett. 30: 1885-1888.

Baidoo et al., 1990, "Synthesis of a Diaminodithiol Bifunctional Chelating Agent for Incorporation of Technetium-99m into Biomolecules", Bioconjugate Chem. 1: 132-137.

Taylor et al., 1990, "Brain Uptake and Retention of [Tc-99m]T691: A Potential New Tracer of Cerebral Blood Flow", J. Nucl. Med. 32: 885 (Abst.).

Knight et al., 1990, "Thrombus Imaging with Tc-99m Synthetic peptides Reactive with Activated Platelets", J. Nucl. Med. 31: 757 #209.

Schwartz et al., 1991, "Preparation of Hydrazino-Modified Proteins and Their Use for the Synthesis of $^{99m}$Tc-Protein Conjugates". Bioconjugate Chem. 2: 333.

Bryson et al., 1990, "Protecting Groups inb the Preparation of Thiolate Complexes of Technetium", Inorg. Chem. 29: 2948-2951.

Kwekkeboom et al., 1991, "[In-111-DTPA-D-Phe]$^1$-Octreotide Scintigraphy in Neuro-endocrine Tumors", J. Nucl. Med. 32: 981, Abstract #305.

Albert et al., 1991, "A Somatostatin Ananlogue to Image SS-Receptor-Positive Tumors: [$^{111}$In-DTPA-DPhe]$^1$-Octreotide (SDZ 215-811)", Abstract LM10, 12th American Peptide Symposium.

Cox et al., 1991, "Technetium Labeled Somatostatin: A Potential Agent for In Vivo Tumor Localization", Abstract, 7th International Symposium on Radiopharmacology, p. 16.

Babich et al., 1993, "Technetium-99m-Labeled Hydrazino Nicotinamide Derivatized Chemotactic Peptide Analogs for Imaging Focal Sites of Bacterial Infection", J. Nucl. Med. 34: 1964-1974.

* cited by examiner

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 19
        (D) OTHER INFORMATION: /label= Amide
            /note= "The carboxyl terminus is modified to an
            amide"

(xi) SEQUENCE DESCRIPTION: SEQ ID NO:1:

Gly Gly Cys Ser Ile Pro Pro Glu Val Lys Phe Asn Lys Pro Phe Val
1               5                   10                  15

Tyr Leu Ile (2) INFORMATION FOR SEQ ID NO:2:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:2:

Gly Gly Cys Ser Ile Pro Pro Glu Val Lys Phe Asn Lys Pro Phe Val
1               5                   10                  15

Tyr Leu Ile (2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:3:

Gly Gly Cys Gly Leu Phe
1               5

(2) INFORMATION FOR SEQ ID NO:4:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 19
        (D) OTHER INFORMATION: /label= Amide
            /note= "The carboxyl terminus is modified to an
            amide"

(xi) SEQUENCE DESCRIPTION: SEQ ID NO:4:

Arg Gly Cys Ser Ile Pro Pro Glu Val Lys Phe Asn Lys Pro Phe Val
1               5                   10                  15
Tyr Leu Ile (2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:5:

Arg Gly Cys Gln Ala Pro Leu Tyr Lys Lys Ile Ile Lys Lys Leu
1               5                   10                  15
Leu Glu Ser (2) INFORMATION FOR SEQ ID NO:6:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 30
        (D) OTHER INFORMATION: /label= Amide
            /note= "The carboxyl terminus is modified to an
            amide"

(xi) SEQUENCE DESCRIPTION: SEQ ID NO:6:

Arg Gly Cys Gly His Arg Pro Leu Asp Lys Lys Arg Glu Glu Ala Pro
1               5                   10                  15
Ser Leu Arg Pro Ala Pro Pro Pro Ile Ser Gly Gly Tyr Arg
            20                  25                  30

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /label= Amide
            /note= "The carboxyl terminus is modified to an
            amide"

(xi) SEQUENCE DESCRIPTION: SEQ ID NO:7:

Gly Gly Cys Arg Pro Lys Pro Gln Gln Phe Phe Gly Leu Met
1               5                   10

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear

```
        (ii) MOLECULE TYPE: peptide (ix) FEATURE:
              (A) NAME/KEY: Modified-site
              (B) LOCATION: 7
              (D) OTHER INFORMATION: /label= D-Phe
                   /note= "The phenylalanine residue is in the D-
                   stereochemical configuration"

(ix) FEATURE:
              (A) NAME/KEY: Modified-site
              (B) LOCATION: 9
              (D) OTHER INFORMATION: /label= D-Trp
                   /note= "The tryptophan residue is in the D-
                   stereochemical configuration"

(ix) FEATURE:
              (A) NAME/KEY: Modified-site
              (B) LOCATION: 13
              (D) OTHER INFORMATION: /label= Amide
                   /note= "The carboxyl terminus is modified to an
                   amide"

(xi) SEQUENCE DESCRIPTION: SEQ ID NO:8:

Ala Lys Cys Gly Gly Gly Phe Tyr Trp Lys Thr Phe Thr
1               5                   10

(2) INFORMATION FOR SEQ ID NO:9:

(i) SEQUENCE CHARACTERISTICS:
              (A) LENGTH: 8 amino acids
              (B) TYPE: amino acid
              (D) TOPOLOGY: linear (ii) MOLECULE TYPE: peptide (ix) FEATURE:
              (A) NAME/KEY: Modified-site
              (B) LOCATION: 8
              (D) OTHER INFORMATION: /label= Amide
                   /note= "The carboxyl terminus is modified to an
                   amide"

(xi) SEQUENCE DESCRIPTION: SEQ ID NO:9:

Gly Gly Cys Phe Val Tyr Leu Ile
1               5
```

MONOAMINE, DIAMIDE, THIOL-CONTAINING METAL CHELATING AGENTS

This application is a continuation-in-part of U.S. patent application Ser. No. 07/807,062, now U.S. Pat. No. 5,443,815 filed Nov. 27, 1991. This application is also a continuation-in-part of U.S. Ser. No. 08/092,355, filed Jul. 15, 1993; and a continuation-in-part of U.S. Ser. No. 08/095,760, filed Jul. 21, 1993 and now U.S. Pat. No. 5,620,675

BACKGROUND OF THE INVENTION

1. Field of the Invention

This invention relates to compositions of matter that are reagents for preparing radiopharmaceuticals, methods for preparing radiopharmaceuticals using said reagents, the radiopharmaceuticals thus prepared, and methods for using such radiopharmaceuticals. In particular, the invention pertains to reagents that are monoamine, diamide, thiol-containing (MADAT) metal chelators, as well as conjugates between said metal chelating groups and a variety of specific targeting moieties. Also provided in one aspect of the invention are radiodiagnostic agents comprised of the metal chelators conjugated with specific targeting moieties and radiolabeled with gamma radiation-emitting radioisotopes. In another aspect are provided radiotherapeutic agents comprised of the metal chelators conjugated with specific targeting moieties and radiolabeled with cytotoxic radioisotopes. Kits comprising the radiopharmaceuticals of the invention and adjuvant agents for the preparation of the radiodiagnostic and radiotherapeutic agents of the invention are provided. Radiodiagnostic and radiotherapeutic methods for using the agents of the invention are also provided.

2. Description of the Prior Art

It is frequently clinically advantageous for a physician to be able to localize the site of a pathological condition in a patient using non-invasive means. Such pathological conditions include diseases of the lungs, heart, liver, kidneys, bones and brain, as well as cancer, thrombosis, pulmonary embolism, infection, inflammation and atherosclerosis.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site or, alternatively, the radiotracer is chosen specifically not to localize at such pathological sites. In many situations it is a particular advantage to use a radiolabeled specific binding compound as a radiopharmaceutical, which localizes specifically to the pathological site in vivo.

A variety of radionuclides are known to be useful for radioimaging, including $^{67}Ga$, $^{99m}Tc$ (Tc-99m), $^{111}In$, $^{123}I$, $^{125}I$, and $^{169}Yb$. However, a number of factors must be considered for optimal radioimaging in humans. To maximize the efficiency of detection, a radionuclide that emits gamma energy in the 100 to 200 keV range is preferred. To minimize the absorbed radiation dose to the patient, the radioisotope should emit no alpha or beta particle radiation, and the physical half-life of the radionuclide should be as short as the imaging procedure will allow. To allow for examinations to be performed on any day and at any time of the day, it is advantageous to have a source of the radionuclide always available at the clinical site.

Tc-99m is the preferred radionuclide for scintigraphic imaging because it has no significant particulate radiation emissions and emits gamma radiation at about 140 keV, it has a physical half-life of 6 hours, and it is readily available on-site using a molybdenum-99/technetium-99m generator.

Other radionuclides used in the prior art are less advantageous than Tc-99m. This can be because the physical half-life of such radionuclides are longer, resulting in a greater amount of absorbed radiation dose to the patient (e.g., indium-111). Alternatively, the gamma radiation energies of such alternate radionuclides are significantly lower (e.g., iodine-125) or higher (e.g., iodine-131) than Tc-99m and are thereby inappropriate for quality scintigraphic imaging. Lastly, many disadvantageous radionuclides cannot be produced using an on-site generator.

Tc-99m is a transition metal that is advantageously chelated by a metal chelator or metal chelating moiety. Chelating moieties capable of binding Tc-99m can be covalently linked to various tarfeting molecules to provide a means for radiolabeling such targeting molecules. This is because the most commonly available chemical species of Tc-99m, pertechnetate ($TcO_4^-$), cannot bind directly to most targeting molecules strongly enough to be useful as a radiopharmaceutical. Complexing of Tc-99m with such radiolabel chelating moieties typically entails chemical reduction of the pertechnetate using a reducing agent such as stannous chloride.

The use of chelating agents for complexing Tc-99m is known in the prior art.

Byrne et al., U.S. Pat. No. 4,434,151 describe $N_2S_2$, homocysteine-containing chelating agents for Tc-99m.

Fritzberg, U.S. Pat. No. 4,444,690 describes a series of bisamide, bisthiol chelating agents for Tc-99m.

Byrne et al., U.S. Pat. No. 4,575,556 describe $N_2S_2$, homocysteine-containing chelating agents for Tc-99m.

Nosco et al., U.S. Pat. No. 4,925,650 describe Tc-99m chelating complexes.

Kondo et al., European Patent Application, Publication No. 483704 A1 disclose a process for preparing a Tc-99m complex with a mercapto-Gly-Gly-Gly moiety.

European Patent Application No. 84109831.2 describes bisamido, bisthiol Tc-99m ligands and salts thereof as renal function monitoring agents.

Burns et al., 1985, European Patent Application No. 85104959.3 describe bisamino, bisthiol compounds for preparing Tc-99m labeled brain imaging agents.

European Patent Application No. 86100360.6 describes dithiol, diamino, or diaminocarboxylic acids or amine complexes for making Tc-99m labeled imaging agents.

Kung et al., 1986, European Patent Application No. 86105920.2 describe bisamino, bisthiol compounds for making small, neutral Tc-99m brain imaging agents.

Bergstein et al., 1988, European Patent Application No. 88102252.9 describe bisamino, bisthiol compounds for making small, neutral Tc-99m imaging agents.

PCT International Patent Application Publication No. WO89/12625 describe bifunctional chelating complexes of bisamido, bisthiol ligands and salts thereof, for use as renal function monitoring agents.

Davison et al., 1981, *Inorg. Chem.* 20: 1629–1632 disclose oxotechnetium chelate complexes.

Fritzberg et al., 1982, *J. Nucl. Med.* 23: 592–598 disclose a Tc-99m chelating agent based on N,N'-bis(mercaptoacetyl)-2,3-diaminopropanoate.

Byrne et al., 1983, *J. Nucl. Med.* 24: P126 describe homocysteine-containing Tc-99m chelating agents.

Bryson et al., 1988, *Inorg. Chem.* 27: 2154–2161 describe neutral complexes of technetium-99 which are unstable to excess ligand.

Misra et al., 1989, *Tet. Lett.* 30: 1885–1888 describe bisamine bisthiol compounds for radiolabeling purposes.

Bryson et al., 1990, *Inorg. Chem.* 29: 2948–2951 describe chelators containing two amide groups, a thiol group and a substituted pyridine group, said chelators forming neutral Tc-99m complexes.

Taylor et al., 1990, *J. Nucl. Med.* 31: 885 (Abst.) describe a neutral Tc-99m complex for brain imaging.

Targeting molecules labeled with radioisotopes have been used as radiopharmaceuticals for both diagnostic and therapeutic purposes. A number of methods have been developed to label targeting molecules with radioisotopes. Particularly important are the isotopes of technetium for scintigraphic imaging and rhenium and tin for therapeutic purposes. Toward this end there have been many examples of chelating groups developed for labeling targeting molecules.

Hnatowich, U.S. Pat. No. 4,668,503 describe Tc-99m protein radiolabeling.

Tolman, U.S. Pat. No. 4,732,684 describe conjugation of targeting molecules and fragments of the metal-binding protein, metallothionein.

Ege et al., U.S. Pat. No. 4,832,940 teach radiolabeled peptides for imaging localized T-lymphocytes.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Morgan et al., U.S. Pat. No. 4,986,979 disclose methods for imaging sites for inflammation.

Fritzberg et al., U.S. Pat. No. 5,091,514 describe various S-protected mercaptoacetylglycylglycine-based chelators for labeling proteins.

Gustavson et al., U.S. Pat. No. 5,112,953 disclose Tc-99m chelating agents for radiolabeling proteins.

Kasina et al., U.S. Pat. No. 5,175,257 describe various combinations of targeting molecules and Tc-99m chelating groups.

Dean et al., U.S. Pat. No. 5,180,816 disclose methods for radiolabeling a protein with Tc-99m via a bifunctional chelating agent.

Flanagan et al., U.S. Pat. No. 5,248,764 describe conjugates between a radiolabel chelating moiety and atrial natiuretic factor-derived peptides.

Reno and Bottino, European Patent Application 87300426.1 disclose radiolabeling antibodies with Tc-99m.

Ranby et al., 1988, International Patent Application No. PCT/US88/02276 disclose a method for detecting fibrin deposits in an animal comprising covalently binding a radiolabeled compound to fibrin.

Dean et al., International Patent Application, Publication No. WO89/12625 teach bifunctional coupling agents for Tc-99m labeling of proteins.

Schoemaker et al., International Patent Application, Publication No. WO90/06323 disclose chimeric proteins comprising a metal-binding region.

Morgan et al., International Patent Application, Publication No. WO90/10463 disclose methods for imaging sites of inflammation.

Flanagan et al., European Patent Application No. 90306428.5 disclose Tc-99m labeling of synthetic peptide fragments via a set of organic chelating molecules.

Gustavson et al., International Patent Application, Publication No. WO91/09876 disclose Tc-99m chelating agents for radiolabeling proteins.

Rodwell et al., 1991, International Patent Application No. PCT/US91/03116 disclose conjugates of "molecular recognition units" with "effector domains.

Cox, International Patent Application No. PCT/US92/04559 discloses radiolabeled somatostatin derivatives containing two cysteine residues.

Rhodes et al., International Patent Application, Publication No. WO93/12819 teach peptides comprising metal ion-binding domains.

Lyle et al., International Patent Application, Publication No. WO93/15770 disclose Tc-99m chelators and peptides labeled with Tc-99m.

Coughlin et al, International Patent Application, Publication No. WO93/21151 disclose bifunctional chelating agents comprising thiourea groups for radiolabeling targeting molecules.

Knight et al., 1990, 37th Annual Meeting of the Society of Nuclear Medicine, Abstract #209, disclose thrombus imaging using Tc-99m labeled peptides.

Babich et al., 1993, *J. Nucl. Med.* 34: 1964–1974 describe Tc-99m labeled peptides comprising hydrazinonicotinamide derivatives.

Well-studied members of the class of chelating groups used for radiolabeling targeting molecules include diamide dithiols (DADS), also known as $N_2S_2$ chelators, and mercaptoacetyltriglycines ($MAG_3$), also known as $N_3S$ chelators. Both of these types of chelating groups form stable chelators with technetium, and methods have been developed to link these chelators to targeting molecules.

Fritzberg, European Patent Application No. 853042255.4 disclose N/S complexes of technetium.

Fritzberg et al., European Patent Application No. 88104755.9 disclose N/S chelating agents.

In general, these methods require that the chelate be heated briefly (15 min) at 100° C. in solution to produce the stable chelate (see, for example, Fritzberg et al., 1986, European Patent Application No. 853042255.4). Since many targeting molecules such as peptides and carbohydrates are labile to heat, producing degradation and inactive side products, there is a need for a labeling technology performed under milder (e.g., room temperature) conditions, that avoids these conventional harsh labeling conditions, and can be completed rapidly in the hospital clinic prior to patient administration. Rapid labeling in a clinical setting is particularly important since many patients require diagnostic information quickly because of the acute nature of their condition.

Another class of chelating compounds developed for labeling targeting molecules are the bisamine bisthiols (termed BATs).

Baidoo et al., U.S. Pat. Nos. 5,196,515 and 5,095,111 disclose bisamine bisthiol complexes.

Kung et al., European Application No. 86105920.2 disclosed bisamine bisthiol ligands and their technetium-99m complexes.

Misra et al., 1989, *Tet. Lett.* 30: 1885–1888 describe bisamine bisthiol compounds for radiolabeling purposes.

Baidoo et al., 1990, *Bioconjugate Chem.* 1: 132–137 describe a method for labeling biomolecules using a bisamine bisthiol.

These compounds are useful when attached to targeting molecules since they can be labeled with technetium at room temperature. Such mild labeling conditions expose chemically-sensitive targeting molecules to a minimum of chemical stress, resulting in less degradation and more chemically pure radiolabeled targeting compounds. However, BAT chelates also have several drawbacks. One drawback of BAT chelators is that these chelates are intrinsically highly lipophilic. This property can cause these compounds to be retained in peripheral blood in excess, interfering with efficient scintigraphy because imaging agents must clear from the peripheral blood to reduce background radioactivity before a useful diagnostic image can be obtained. This drawback may alone be important enough to determine whether a BAT chelator-containing scintigraphic imaging agent is a commercially feasible product.

Another drawback of BAT chelators is that it is difficult to develop the chemistry to covalently attach such chelates to the targeting molecules. Although successful covalent linkage of BAT chelators to targeting molecules has been achieved, it has also typically resulted in the production of costly intermediates and has proven ultimately to be a costly way to produce the final radiopharmaceutical product.

The use of chelating agents for radiolabeling peptides, and methods for labeling peptides with Tc-99m are known in the prior art and are disclosed in co-pending U.S. patent application Ser. Nos. 07/653,012, 07/807,062, 07/871,282, 07/886,752, 07/893,981, 07/955,466, 08/019,864, 08/073,577, 08/210,822, 08/236,402 and 08/241,625, and radiolabeled peptides for use as scintigraphic imaging agents for imaging thrombi are known in the prior art and are disclosed in co-pending U.S. patent application Ser. Nos. 07/886,752, 07/893,981 and 08/044,825 and International Patent Applications Serial Nos. PCT/US92/00757, PCT/US92/10716, PCT/US93/02320, PCT/US93/03687, PCT/US93/04794, PCT/US93/05372, PCT/US93/06029, PCT/US93/09387, PCT/US94/01894, PCT/US94/03878, and PCT/US94/05895, each of which are hereby incorporated by reference in its entirety.

There exists a need for radiopharmaceuticals for diagnostic and therapeutic purposes that can be easily radiolabeled under mild chemical conditions to avoid chemical and physical degradation of labile biological targeting molecules. There remains a need for low-cost chelating groups which are easy to synthesize, moderately lipophilic, and can be linked to a targeting molecule and subsequently labeled with Tc-99m quickly at room temperature.

SUMMARY OF THE INVENTION

The present invention provides reagents useful in preparing diagnostic and therapeutic radiopharmaceutical agents. Specifically, the invention provides reagents that are monoamine, diamide, thiol-containing (MADAT) metal chelators. The invention also provides monoamine, bisamide, monothiol chelators and complexes of such metal chelators with isotopes of technetium-99m, rhenium-186, rhenium-188, tin-117m, copper-64 and copper-67. Conjugates between said metal chelating groups and a variety of specific targeting moieties are also provided. Such conjugates are comprised of a metal chelating group of the invention covalently linked to a specific targeting molecule. Such radiolabeled conjugates comprise the radiodiagnostic and radiotherapeutic agents provided by the invention.

The invention provides radiopharmaceutical agents and reagents for preparing such radiopharmaceuticals comprising a targeting moiety covalently linked to a metal chelator selected from the group consisting of:

(i) a group having the formula:

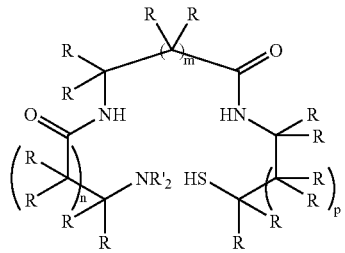

(ii) a group having the formula:

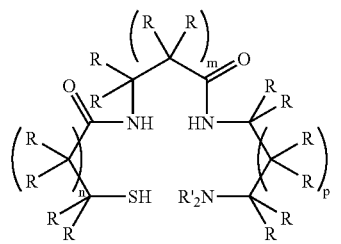

II wherein n, m and p are each integers that are independently 0 or 1; each R' is independently H, lower alkyl, $C_2$–$C_4$ hydroxyalkyl, or $C_2$–$C_4$ alkoxyalkyl, and each R is independently H or R", where R" is substituted or unsubstituted lower alkyl or phenyl not comprising a thiol group, and one R or R' is L, where L is a bivalent linker moiety linking the metal chelator to the targeting moiety and wherein when one R' is L, $NR'_2$ is an amine.

In preferred embodiments, L is a $C_1$–$C_6$ linear, branched chain or cyclic alkyl group, a carboxylic ester, a carboxamide, a sulfonamide, an ether, a thioether, an amine, an alkene, an alkyne, a 1,2-, 1,3- or 1,4-linked, optionally substituted, benzene ring, or an amino acid or peptide of 2 to about 10 amino acids, or combinations thereof.

In preferred embodiments, R" is a $C_1$–$C_6$ linear, branched or cyclic alkyl group; a $C_qOC_r$-, -$C_qNHC_r$- or -$C_qSC_r$- group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, hydroxyl, substituted amine, guanidine, amidine, substituted thiol, ether, phosphate, or sulfate group; an indole group; a $C_1$–$C_6$ heterocyclic group containing 1 to 3 nitrogen, oxygen or sulfur atoms or combinations thereof.

Preferred metal chelators of the invention include chelators having the formula:

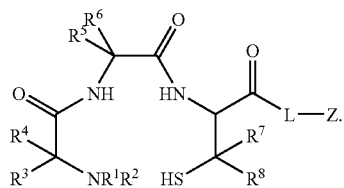

III wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group; $R^7$ and $R^8$ are each independently H, lower alkyl, lower hydroxyalkyl or lower alkoxyalkyl; L is a bivalent linker group and Z is a targeting moiety.

Additional preferred metal chelators of the invention include chelators of formula:

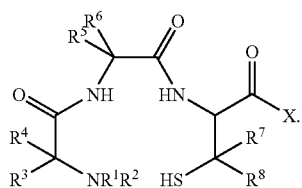

IV wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group, and one of $R^3$, $R^4$, $R^5$ or $R^6$ is Z-L-HN(CH$_2$)$_n$—, where L is a bivalent linker group, Z is a targeting moiety, and n is an integer from 1 to 6; $R^7$ and $R^8$ are each independently H, lower alkyl, lower hydroxyalkyl or lower alkoxyalkyl; and X is an amino group, a substituted amino group or —NR$^1$-Y, where Y is an amino acid, an amino acid amide, or a peptide comprising from 2 to 10 amino acids.

More preferred metal chelators of the invention include chelators having the formula:

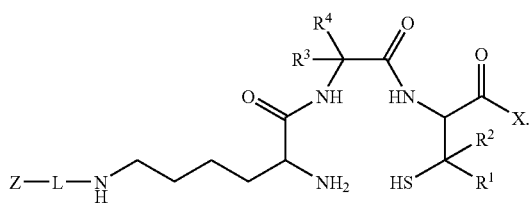

V wherein $R^1$ and $R^2$ are each independently H, lower alkyl, lower hydroxyalkyl, or lower alkenylalkyl; $R^3$ and $R^4$ are independently H, substituted or unsubstituted lower alkyl or phenyl not comprising a thiol group; n is an integer from 1 to 6; L is a bivalent linker group; and Z is a targeting moiety.

Additional more preferred metal chelators include chelators of formula:

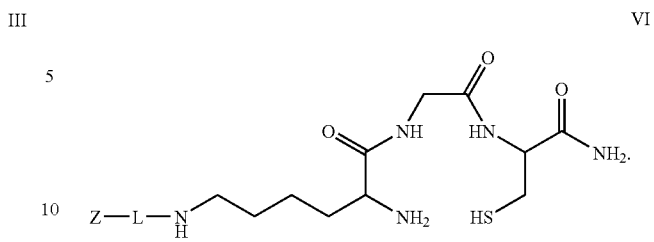

VI wherein L is a bivalent linker group and Z is a targeting moiety.

Most preferred metal chelators of the invention include chelators having the following formulae:
  (amino acid)$^1$-(amino acid)$^2$-cysteine-,
  (amino acid)$^1$-(amino acid)$^2$-isocysteine-,
  (amino acid)$^1$-(amino acid)$^2$-homocysteine-,
  (amino acid)$^1$-(amino acid)$^2$-penicillamine-,
  (amino acid)$^1$-(amino acid)$^2$-2-mercaptoethylamine-,
  (amino acid)$^1$-(amino acid)$^2$-2-mercaptopropylamine-,
  (amino acid)$^1$-(amino acid)$^2$-2-mercapto-2-methylpropylamine-,
  (amino acid)$^1$-(amino acid)$^2$-3-mercaptopropylamine-, wherein (amino acid) in a primary α- or β-amino acid not comprising a thiol group and wherein the chelator is attached to either a targeting moiety or a linker group via a covalent bond with the carboxyl terminus of the chelator or a side chain on one of the amino acid groups.

Most preferred chelators also include chelators of the above formula wherein (amino acid)$^1$ is either an α,ω- or β,ω-amino acid wherein the α- or β-amino group is a free amine and the α,ω- or β,ω-amino acid is covalently linked via the ω amino group.

Other most perferred metal chelators include those selected from the group consisting of:
  -cysteine-(amino acid)-(α,ω- or β,ω-diamino acid);
  -isocysteine-(amino acid)-(α,ω- or β,ω-diamino acid);
  -homocysteine-(amino acid)-(α,ω- or β,ω-diamino acid);
  -penicillamine-(amino acid)-(α,ω- or β,ω-diamino acid);
  2-mercaptoacetic acid-(amino acid)-(α,ω- or β,ω-diamino acid);
  2- or 3-mercaptopropionic acid-(amino acid)-(α,ω)- or β,ω-diamino acid);
  2-mercapto-2-methylpropionic acid-(amino acid)-(α,ω- or β,ω-diamino acid); wherein (amino acid) in a primary α- or β-amino acid not comprising a thiol group and wherein the chelator is attached to either a targeting moiety or a linker group via a covalent bond with the amino terminus of the chelator or a side chain on one of the amino acid groups.

Particularily preferred metal chelators are selected from the group consisting of: Gly-Gly-Cys-, Arg-Gly-Cys-, -(ε-Lys)-Gly-Cys-, -(δ-Orn)-Gly-Cys-, -(γ-Dab)-Gly-Cys-, and -(β-Dap)-Gly-Cys-. (In these formulae, it will be understood that: ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

An example of preferred metal chelators of structure type (III) above is the chelator Gly-Gly-Cys- which forms a metal chelating moiety having the structure:

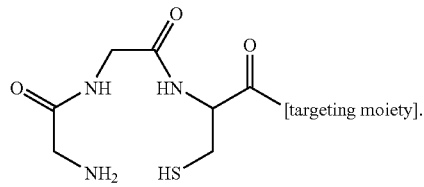

VII

Chelating ligands having structure type VII form oxotechnetium complexes having the structure:

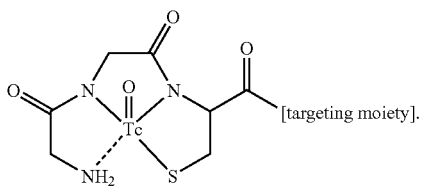

VIII

An example of more preferred metal chelators having structure type V as shown above is Lys-(ω-peptide)-Gly-Cys.amide which forms a metal chelating moiety of structure:

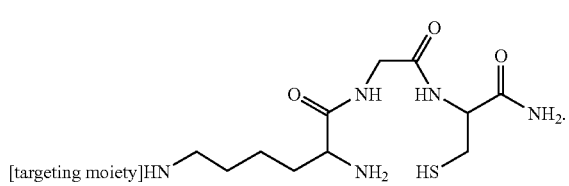

IX

Chelating ligands having structure type IX form oxotechnetium complexes having the structure:

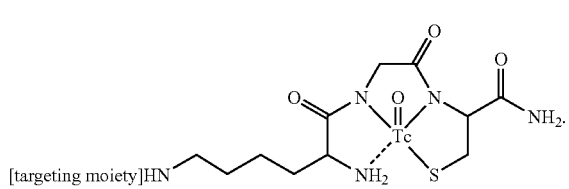

X

An example of a reagent for preparing a radiopharmaceutical agent as provided by this invention comprising a metal chelating group having structure type II as shown above is (targeting moiety)-Cys-Gly-α,β-diaminopropionamide which forms a metal chelating moiety of structure:

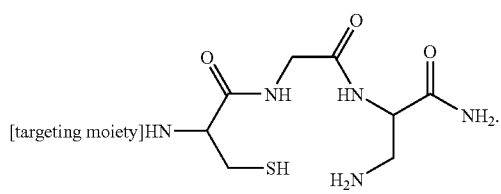

XI

Radiodiagnostic agents having structure type XI form oxotechnetium complexes having the structure:

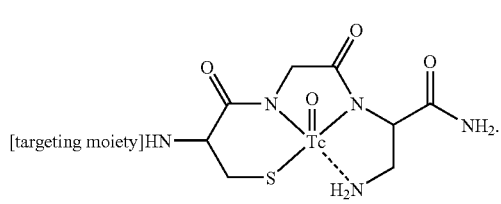

XII

The invention also provides each of the metal chelators of the invention as embodiments of the invention are useful as radiodiagnostic and radiotherapeutic agents when labeled with the appropriate radioisotope and have utility as radiopharmaceuticals as described herein for a number of radiodiagnostic and radiotherapeutic applications, e.g., renal, hepatic and cerebral imaging.

Radiopharmaceutical agents are provided by this invention comprising targeting moieties that are monoclonal antibodies, peptides, receptor binding molecules, adhesion molecules, enzyme substrates, enzyme inhibitors, carbohydrates, oligonucleotides, oligonucleosides and in general any chemical entity having an affinity for some component of a living organism. Examples of targeting moieties include immunoglobulins, F(ab')$_2$ fragments or Fab or Fab' fragments derived from murine, human or chimeric human-murine monoclonal antibodies, somatostatin receptor binding peptides, glycoprotein IIb/IIIa binding peptides, atherosclerotic plaque binding peptides, platelet factor 4 derived peptides, receptor binding molecules, adhension molecules, enzyme substrates, enzyme inhibitors, and carbohydrates.

The radiopharmaceuticals and reagents for preparing such radiopharamceuticals of the invention may be formed wherein the targeting moiety or the metal chelator or both, are covalently linked to a polyvalent linking moiety. Polyvalent linking moieties of the invention are comprised of at least 2 identical linker groups capable of being covalently bonded to targeting moieties or metal chelators. Polyvalent linking moieties are formed from precursor reagents wherein each linking moiety comprises a linker functional group which is capable of reacting with targeting moieties or metal chelators or both. Preferred linker functional groups are primary or secondary amines, hydroxyl groups, carboxylic acid groups or thiol-reactive groups such as maleimides and 2-haloacetyl groups. In preferred embodiments, the polyvalent linking moieties are comprised of bis-succinimidomethylether (BSME), 4-(2,2-dimethylacetyl)benzoic acid (DMAB), tris(succinimidylethyl)amine (TSEA), tris(acetamidoethyl)amine, bis-acetamidomethyl ether, bis-acetamidoethyl ether, α,ε-bis-acetyllysine, lysine and 1,8-bis-acetamido-3,6-dioxa-octane.

The invention provides scintigraphic imaging agents that are radiodiagnostic agents comprised of Tc-99m complexes of the metal chelating group/targeting moiety conjugates of the invention. Methods for radiolabeling such compounds are also provided. Radiolabeled complexes provided by the invention are formed by reacting the conjugate reagents of the invention with Tc-99m in the presence of a reducing agent. Preferred reducing agents include but are not limited to dithionite ion, stannous ion, and ferrous ion. Complexes of the invention are also formed by labeling the conjugate reagents of the invention with Tc-99m by ligand exchange with a prereduced Tc-99m complex as provided herein.

The invention also provides kits for preparing the Tc-99m labeled radio-pharmcaceutical agents of the invention. Kits for Tc-99m labeling the conjugate reagents of the invention are comprised of a sealed container (e.g. a vial or a syringe) containing a predetermined quantity of a conjugate reagent of the invention and a sufficient amount of reducing agent to label the reagent with Tc-99m.

This invention provides methods for producing the metal chelators, metal chelator/targeting moiety conjugate reagents and radiopharmaceutical agents of the invention by chemical synthesis in vitro. In a preferred embodiment, such compounds are synthesized by solid phase peptide synthesis.

This invention also provides methods for using the radiodiagnostic and radiotherapeutic agents of the invention. In one embodiment, scintigraphic imaging agents of the invention are provided that are Tc-99m labeled radiopharmaceuticals for imaging sites within a mammalian body by obtaining in vivo gamma scintigraphic images. These methods comprise administering an effective diagnostic amount of a Tc-99m radiolabeled radiodiagnostic conjugate reagent of the invention and detecting the gamma radiation emitted by the Tc-99m localized at the site within the mammalian body.

In another aspect are provided radiotherapeutic agents that are Re-186, Re-188, Sn-117m or Cu-67 labeled radiopharmaceuticals for localizing cytotoxic amounts of such radioisotopes at a pathological site in vivo. These methods comprise administering an effective therapeutic amount of a radiolabeled radiotherapeutic conjugate reagent of the invention and allowing said radiopharmaceutical to localize at the appropriate pathological site to have a therapeutic effect by cytotoxicity at that site.

Specific preferred embodiments of the present invention will become evident from the following more detailed description of certain preferred embodiments and the claims.

DETAILED DESCRIPTION OF PREFERRED EMBODIMENTS

The present invention provides monoamine, diamide, thiol-containing (MADAT) metal chelators and embodiments of such chelators complexed with radioisotopes, including technetium-99m, rhenium-186, rhenium-188, tin-117, copper-64 and copper-67. The invention provides radiopharmaceutical agents, including radiodiagnostic agents and radiotherapeutic agents, that are the metal chelators of the invention complexed with radioisotopes appropriate for diagnostic and therapeutic applications. Methods of making said metal chelators, methods of complexing said metal chelators with radioisotopes, and methods of using such metal chelators as radiopharmaceuticals are also provided by the invention.

The present invention also provides monoamine, diamide, thiol-containing metal chelators covalently linked to targeting moieties to provide reagents for preparing radiopharmaceuticals capable of binding to or accumulating at sites in a mammalian body. In certain embodiments of this aspect of the invention, the metal chelator and the targeting moiety are directly chemically linked by a covalent bond. In other embodiments, the metal chelator and the targeting moiety are linked via a linker which in certain embodiments comprises an amino acid or peptide. Complexes of the metal chelate/targeting moiety conjugates of the invention with radioisotopes, including technetium-99m, rhenium-186, rhenium-188, tin-117m, copper-64 and copper-67, are also provided. The invention provides radiopharmaceutical agents, including radiodiagnostic agents and radiotherapeutic agents, that are the metal chelator/targeting moiety conjugates of the invention complexed with radioisotopes appropriate for diagnostic and therapeutic applications. Methods of making said conjugates, methods of complexing said conjugates with radioisotopes, and methods of using such conjugates as radiopharmaceuticals are also provided by the invention.

Radiopharmaceutical agents are thus also provided by the invention, comprising the metal chelator/targeting conjugates of the invention complexed with radioisotopes. In one aspect, the invention provides radiodiagnostic agents including scintigraphic imaging agents for imaging target sites within a mammalian body wherein the radiopharamceutical comprises a metal chelate of Tc-99m. In another aspect, the invention provides radiotherapeutic agents for directing cytotoxic amounts of radioisotopes such as Re-186, Re-188, Sn-117m, Cu-64 and Cu-67 to pathological sites within a mammalian body.

In radiodiagnostic agents such as scintigraphic imaging agents as provided by this invention, labeling with Tc-99m is advantageous because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator.

For purposes of this invention, the term "targeting moiety" is intended to mean any compound that binds to or accumulates at a target site in a mammalian body, i.e., the compound localizes to a greater extent at the target site that to surrounding tissues. This is advantageous in radiodiagnostic embodiments of the invention because scintigraphic imaging agents comprising such targeting moieties are distributed within a mammalian body after administration to provide visual definition of the target in vivo. This is advantageous in radiotherapeutic embodiments of the invention because the radiocytotoxic agents are thus localized at a pathological site with concomitant minimization of non-specific systemic toxicity in vivo.

Radiopharmaceutical agents and reagents for their preparation are provided by this invention comprising targeting moieties that are monoclonal antibodies, peptides, receptor binding molecules, adhesion molecules, enzyme substrates, enzyme inhibitors, carbohydrates, oligonucleotides, oligonucleosides and in general any chemical entity having an affinity for some component of a living organism. Examples of targeting moieties include immunoglobulins, F(ab')$_2$ fragments or Fab or Fab' fragments derived form murine, human or chimeric human-murine monoclonal antibodies; somatostatin receptor binding peptides such as cyclo(N—CH$_3$)-Phe-Tyr-(D-Trp)-Lys-Val-Hcy-; glycoprotein IIb/IIIa binding peptides such as CH$_2$CO.(D-Tyr)-Amp-Gly-Asp-Cys-Lys-Gly-Cys-Gly.amide; atherosclerotic plaque binding peptides such as Arg-Ala-Leu-Val-Asp-Thr-Leu-Lys-Phe-Val-Thr-Gln-Ala-Glu-Gly-Ala-Lys.amide; platelet factor 4 derived peptides such as Pro-Leu-Tyr-Lys-Lys-Ile-Ile-Lys-Lys-Leu-Leu-Glu-Ser; receptor binding molecules such as spiroperidol and haloperidol; adhesion molecules such as asialyl Lewis$^x$; enzyme substrates such as 2-nitroimidazole; enzyme inhibitors such as hirudin and D-Phe-Pro-Arg-chloromethylketone; and carbohydrates such as β-glucans.

In certain embodiments of the reagents of the invention, β-glucans comprise the targeting moiety. For the purposes of this invention, the term β-glucan is intended to mean oligosccharides comprising 1,3- and 1,6-linked β-D-glucose residues wherein the β-glucan moiety has a molecular weight of up to about 2,000 kilodaltons. A preferred embodiment of β-glucan-containing reagent of the invention has formula:

β-glucan-(=NNHCO.(CH$_2$)$_3$CO.)(ε-K)GCY.amide.

In embodiments of this invention wherein the targeting moiety is a peptide, each peptide embodiment of the invention is comprised of a sequence of amino acids. The term amino acid as used in this invention is intended to include all L- and D-, primary α- and β-amino acids, naturally occurring, modified, substituted, altered and otherwise. Peptides comprising targeting moieties of the invention include but are not limited to peptides of the following formulae:

(DTPA).Nal$_D$.Cpa.YW$_D$KT.Nal.T(ε-K)GCKK.amide
F$_D$.Cpa.YW$_D$K.Abu.Nal.T(ε-K)GC.amide
CH$_2$CO.FFW$_D$KTFC(ε-K)GC.amide
cyclo(N—CH$_3$)FYW$_D$KV.Hcy.(CH$_2$CO.(ε-K)GC.amide)
GGCSIPPEVKFNKPFVYLIamide(SEQ. ID NO. 1)
GGCSIPPEVKFNKPFVYLIamide(SEQ. ID NO. 2)
GGCGLF(SEQ. ID NO. 3)
RGCSIPPEVKFNKPFVYLIamide(SEQ. ID NO. 4)
RGCQAPLYKKIIKKLLES(SEQ. ID NO. 5)
RGCGHRPLDKKREEAPSLRPAPPPISGGYRamide (SEQ. ID NO. 6)
GGCRPKPQQFFGLMamide(SEQ. ID NO. 7)
AKCGGF$_D$YW$_D$KTFTamide(SEQ. ID NO. 8)
GGCFVYLI.amide(SEQ. ID NO. 9)
acetyl.F$_D$FYW$_D$KTFT(ε-K)GC.amide
(DTPA).F$_D$FYW$_D$KTFT(ε-K)GC.amide
acetyl.F$_D$FYW$_D$KTFTGGG(ε-K)GC.amide
(DTPA).(ε-K)GCF$_D$FYW$_D$KTFT.amide
acetyl.F$_D$FYW$_D$KTFTGGG(ε-K)KC.amide
F$_D$.Cpa.YW$_D$KTFTGGG(ε-K)GC.amide
(DTPA).F$_D$.Cpa.YW$_D$KTFT(ε-K)GC.amide
(DTPA).Nal$_D$.Cpa.YW$_D$KTFT(ε-K)GC.amide
(DTPA).Aca.F$_D$.Cpa.YW$_D$KTFT(ε-K)GC.amide
cyclo(N—CH$_3$)FYW$_D$KV.Hcy.(CH$_2$CO.K(ε-K)GC.amide)
(DTPA).Nal$_D$.Cpa.YW$_D$KTFT(ε-K)GCKK.amide
acetyl.KKKKK.Nal$_D$.Cpa.YW$_D$KTFT(ε-K)GC.amide
CH$_2$CO.FFW$_D$KTFCKKKKK(ε-K)GC.amide
CH$_2$CO.FFW$_D$KTFC(ε-K)KKKKKGC.amide
DDDD.Nal$_D$.Cpa.YW$_D$KTFT(ε-K)GCKKKK.amide
Nal$_D$.Cpa.YW$_D$KTFT(ε-K)GCKK.amide
(2-ketogulonyl).F$_D$.Cpa.YW$_D$KTFT(ε-K)GC.amide
KDKD.Nal$_D$.Cpa.YW$_D$KTFT(ε-K)GCKDKD.amide
acetyl.KKKKK.Nal$_D$.Cpa.YW$_D$KTFT(ε-K)GCKK.amide
acetyl.Nal$_D$.Cpa.YW$_D$KTFT(ε-K)GCKK.amide
KKKK.Nal$_D$.Cpa.YW$_D$KTFT(ε-K)GCDDDD amide
(2-ketogulonyl).Nal$_D$.Cpa.YW$_D$KTFT(ε-K)GCKK.amide
Trc.Nal$_D$.Cpa.YW$_D$KTFT(ε-K)GCKK.amide
Hca.Nal$_D$.Cpa.YW$_D$KTFT(ε-K)GCKK.amide
(Trc)$_2$.Nal$_D$.Cpa.YW$_D$KTFT(ε-K)GCKK.amide
K$_D$KKK.Nal$_D$.Cpa.YW$_D$KTFT(ε-K)GCDD.amide
K$_D$DKD.Nal$_D$.Cpa.YW$_D$KTFT(ε-K)GCKDKD.amide
cyclo(N—CH$_3$)FYW$_D$KV.Hcy.(CH$_2$CO.KKKKK(ε-K) GC.amide
acetyl.KK(ε-K)GCGCGGPLYKKIIKKLLES F$_D$.Cpa.YW$_D$KTFT(ε-K)GCR.amide
(Trc-imide).Nal$_D$.Cpa YW$_D$KTFT(ε-K)GCR.amide
Trc.(Trc-imide).K.Nal$_D$.Cpa.YW$_D$KTFT(ε-K)GCRR.amide
(Trc-imide)$_2$K.Nal$_D$.Cpa.YW$_D$KTFT(ε-K)GCR.amide
cyclo(N—CH$_3$)FYW$_D$KV.Hcy.(CH$_2$CO.(ε-K)GCK amide)
(acetyl.TKPRGG)$_2$K(ε-K)GC.amide
acetyl-DDD.Nal$_D$.Cpa.YW$_D$KTFT(ε-K)GCKK.amide
K$_D$KK.Nal$_D$.Cpa.YW$_D$KTFT(ε-K)GCDDD.amide
D$_D$DF$_D$.Cpa.YW$_D$KTFT(ε-K)GCKK.amide
acetyl.D$_D$F$_D$.Cpa.YW$_D$KTFT(ε-K)GCKK.amide
K$_D$KKKF$_D$.Cpa.YW$_D$KTF,Nal.(ε-K)GCDDDD.amide
D$_D$F$_D$.Cpa.YW$_D$KTFT(ε-K)GCKK amide
acetyl.D$_D$F$_D$.Cpa.YW$_D$KTFT(ε-K)GCKK.amide
F$_D$.Cpa.YW$_D$KTFT(ε-K)GCKK.amide
Nal$_D$.Cpa.YW$_D$KTFT(ε-K)GCKK.amide
F$_D$FYW$_D$KTFT(ε-K)GCKK.amide
(CH$_2$CO.Y$_D$.Apc.GDCGGC$_{Acm}$GC$_{Acm}$GGC.amide)$_2$ (CH$_2$CO)$_2$K.(ε-K)GC.amide
(CH$_2$CO.Y$_D$.Apc.GDC)$_2$K.(ε-K)GCG.amide
K$_D$.Nal$_D$.Cpa.YW$_D$KTFT(ε-K)GCD.amide
K$_D$K.Nal$_D$.Cpa.YW$_D$KTFT(ε-K)GCDD.amide
{(CH$_2$CO.Y$_D$.Apc.GDCG)$_2$KG}$_2$.K(ε-K)GCG.amide
{(CH$_2$CO.Y$_D$.Apc.GDCGGCG.amide)(CH$_2$CO)}$_2$. K(ε-K) GC.amide
(CH$_2$CO.Y$_D$.Apc.GDCKKG)$_2$K(ε-K)GC.β-Ala.amide
({(CH$_2$CO.Y$_D$.Apc.GDCGGC$_{Acm}$GC$_{Acm}$GGC.amide) (CH$_2$CO)}$_2$,K)$_2$K(ε-K)GCG.amide
cyclo(N—CH$_3$)FYW$_D$KV.Hcy.(CH$_2$CO.K(ε-K)KCK.amide)
cyclo(N-methyl)FYW$_D$KV.Hcy.(CH$_2$CO.(β-Dap)KCR.amide)
cyclo(N-methyl)FYW$_D$KV.Hcy.(CH$_2$CO.(β-Dap)KCK.amide)
cyclo(N-methyl)FYW$_D$KV.Hcy.(CH$_2$CO.(δ-Orn)GCK.amide)
cyclo(N-methyl)FYW$_D$KV.Hcy.(CH$_2$CO.(β-Dap)GCK.amide)
cyclo(N-methyl)FYW$_D$KV.Hcy.(CH$_2$CO.(ε-K)GCKK.amide)
cyclo(N-CH$_3$)FYW$_D$KV.Hcy.(CH$_2$CO).K(ε-K)GC.amide
(DTPA).Nal$_D$.Cpa.YW$_D$KTFT(ε-K)GCKK.amide
AKCGGGF$_D$YW$_D$KTFT.amide
(DTPA).Nal$_D$.Cpa.YW$_D$KT.Nal.T(ε-K)GCKK.amide
cyclo(N—CH$_3$)FYW$_D$KV.Hcy.(CH$_2$CO).(ε-K)GC.amide
KDKD.Nal$_D$.Cpa.YW$_D$KTFT(ε-K)GCKDKD.amide
(2-ketogulonyl)F$_D$.Cpa.YW$_D$KTFT(ε-K)GC.amide
acetyl.Nal$_D$.Cpa.YW$_D$KTFT(ε-K)GCKK.amide
{(CH$_2$CO.Y$_D$.Apc.GDCGGC$_{Acm}$GC$_{Acm}$GGC.amide)$_2$ (CH$_2$CO)$_2$K}$_2$.K(ε-K)GCG.amide
(CH$_2$CO.Y$_D$.Apc.GDCKGCG.amide)$_2$(CH$_2$CO)$_2$K(ε-K) GC.amide
(CH$_2$CO.Y$_D$.Apc.GDCKGG)$_2$K(ε-K)GC.β-Ala.amide
{(CH$_2$CO.Y$_D$.Apc.GDCG)$_2$KG}$_2$K(ε-K)GCG.amide
(CH$_2$CO.Y$_D$.Apc.GDCGGC$_{Acm}$GC$_{Acm}$GGC.amide)$_2$ (CH$_2$CO)$_2$K(ε-K)GC.amide
cyclo(N—CH$_3$)FYW$_D$KV.Hcy.(CH$_2$CO).(ε-K)GCK.amide
cyclo(N—CH$_3$)FYW$_D$KV.Hcy. (CH$_2$CO.GC.Dap.Dap.amide)
cyclo(N—CH$_3$)FYW$_D$KV.Hcy.(CH$_2$CO.(β-Dap)KCR.amide)
cyclo(N—CH$_3$)FYW$_D$KV.Hcy.(CH$_2$CO.(β-Dap)KCK.amide)
cyclo(N—CH$_3$)FYW$_D$KV.Hcy.(CH$_2$CO.(γ-Dab)KCR.amide)
cyclo(N—CH$_3$)FYW$_D$KV.Hcy.(CH$_2$CO.(δ-Orn)GCK.amide)

cyclo(N-CH$_3$)FYW$_D$KV.Hcy.(CH$_2$CO.(β-Dap)GCK.amide)
acetyl-KKKKKK(ε-K)GCGGPLYKKIIKKLLES
(CH$_2$CO.Y$_D$.Amp.GDC.KGCG.amide)$_2$(CH$_2$CO)$_2$K(ε-K)
GC.amide
(CH$_2$CO.Y$_D$.Amp.GDC.GGC$_{Acm}$GC$_{Acm}$GGC.amide)$_2$
(CH$_2$CO)$_2$K(ε-K)GC.amide.

(Single-letter abbreviations for amino acids can be found in G. Zubay, Biochemistry (2d. ed.), 1988 (MacMillen Publishing: New York) p. 33; other abbreviations are as follows: Acm is acetamidomethyl; Mob is 4-methoxybenzyl; Abu is aminobutyric acid; F$_D$ is D-phenylalanine; W$_D$ is D-tryptophan; Y$_D$ is D-tyrosine; Aca is 6-aminohexanoic acid; Apc is S-(3-aminopropyl)cysteine; Hcy is homocysteine; Nal is 2-naphthylalanine; Cpa is 4-chlorophenylalanine; K$_D$ is D-lysine; D$_D$ is D-aspartate; Nal$_D$ is D-2-naphthylalanine; DTPA is diethylenetriaminepentaacetic acid; Trc is tricarballylic acid; Trc-imide is tricarballylic imide; and Hca is hexacarboxycyclohexane. ( . . . )$_2$K represents covalent linkage to both amino groups of lysine. Hcy( . . . ) represents covalent linkage to the sidechain sulfur atom of homocysteine. (N—CH$_3$)F represents N-α-methylphenylalanine. Underlining between groups (e.g., as between the CH$_2$CO group and cysteine (C) in CH$_2$CO.Y$_D$RGDC) represents a cyclic sulfide. Underlining between amino acids (e.g., as between the cysteines (C) in CNPRGDC) represents a cyclic disulfide bond. The term "cyclo" before an underlined sequence means an N-terminus-to-C-terminus cyclic sequence. The subscript X$_D$ indicates the amino acid is in the D-configuration; all other subscripts refer to amino acid sidechain protecting groups. ε-K represents a lysine residue in which the E-amino group, rather than the typical α-amino group, is covalently linked to the carboxyl group of the adjacent amino acid to form a peptide bond. δ-Orn represents an ornithine residue in which the δ-amino group, rather than the typical α-amino group, is covalently linked to the carboxyl group of the adjacent amino acid to form a peptide bond. γ-Dab represents a 2,4-diaminobutyric acid residue in which the γ-amino group is covalently linked to the carboxyl group of the adjacent amino acid to form a peptide bond. β-Dap represents a 1,3-diaminopropionic acid residue in which the β-amino group is covalently linked to the carboxyl group of the adjacent amino acid to form a peptide bond. This list of reagents for preparing radiopharamaceuticals provided by the invention is illustrative and not intended to be limiting or exclusive, and it will be understood by those with skill in the art that reagents comprising combinations of the peptides disclosed herein or their equivalents may be covalently linked to any of the chelating moieties of the invention and be within its scope, including combinations of various targeting moieties and metal chelators as disclosed herein.

In certain embodiments of the invention, the metal chelators and the targeting moieties are linked via a polyvalent linking moiety. Polyvalent linking moieties are covalently linked to the targeting moieties of the invention, the metal chelators, or both. Polyvalent linking moieties provided by the invention are comprised of a least 2 linker functional groups capable of covalently bonding to targeting moieties or metal chelators. Such functional groups include but are not limited to primary and secondary amines, hydroxyl groups, carboxylic acid groups and thiol reactive groups. Polyvalent linking moieties are comprised of preferably at least three functional groups capable of being covalently linked to targeting moieties or metal chelators. Preferred polyvalent linking moieties include amino acids such as lysine, homolysine, ornithine, aspartic acid and glutamic acid; linear and cyclic amines and polyamines; polycarboxylic acids; and activated thiols such as di- and tri-maleimides. Also preferred are embodiments wherein the polyvalent linking moieties comprise a multiplicity of polyvalent linking moieties covalently linked to form a branched polyvalent linking moiety. Specific preferred polyvalent linking moieties include bissuccinimdylmethylether, 4-(2,2-dimethylacetyl)benzoic acid, tris(succinimidylethyl) amine, 4-(O—CH$_2$CO-Gly-Gly-Cys.amide)acetophenone, bis-succinimidohexane, tris(acetamido-ethyl)amine, tris(acetamidomethyl)ether, bis(acetamidoethyl)ether, α,ε-bisacetyllysine, and 1,8-bis-acetamido-3,6-dioxa-octane.

Peptide targeting moieties of the present invention can be chemically synthesized in vitro. Peptide targeting moieties of the present invention can generally advantageously be prepared on a peptide synthesizer. The peptide targeting moieties of this invention can be synthesized wherein the chelating group is covalently linked to the specific-binding peptide during chemical in vitro synthesis, using techniques well known to those with skill in the art. The incorporation of the chelating group during synthesis of the peptide is particularly advantageous as it provides reagents in which the exact location of the covalent link between the specific-binding peptide and the complexing group is both known and can be designed into the reagent so as to avoid or minimize any perturbation of the specific binding affinity of the specific binding peptide.

In addition, metal chelators may be covalently linked to the groups comprising the side-chains of amino acids, for example, the ε-amino group of lysine, to yield, for example, αN(Fmoc)-Lys-εN-(Gly-Gly-Cys-), which may be incorporated at any position in a peptide chain. This sequence is particularly advantageous as it affords an easy mode of incorporation into a target binding peptide. This invention provides for the incorporation of these chelators into virtually any peptide targeting moiety, resulting in a radiolabeled peptide covalently linked to a Tc-99m complexing moiety.

In forming a complex of radioactive technetium with the metal chelators or metal chelator/targeting moiety conjugates of this invention, a technetium complex, preferably a salt of Tc-99m pertechnetate, is reacted with the chelator or conjugate in the presence of a reducing agent; in a preferred embodiment, the reducing agent is a salt of a stannous ion, most preferably stannous chloride. The scintigraphic imaging agents of the invention which are Tc-99m-labeled metal chelators or metal chelator/targeting moiety conjugates are conveniently and advantageously provided from a kit comprising a sealed vial containing a predetermined quantity of the reagent and a sufficient amount of reducing agent to label the reagent with Tc-99m. Alternatively, scintigraphic imaging agents of the invention may be formed by reacting a metal chelator or metal chelator/targeting moiety conjugate of the invention with a pre-formed labile complex of technetium and another compound known as a transfer ligand. This process is known as ligand exchange and is well known to those skilled in the art. The labile complex may be formed using such transfer ligands as tartrate, citrate, gluconate, glucoheptonate or mannitol, for example. Among the Tc-99m pertechnetate salts useful with the present invention are included the alkali metal salts such as the sodium salt, or ammonium salts or lower alkyl ammonium salts. The reaction of the reagents of this invention with Tc-99m pertechnetate or preformed Tc-99m labile complex can be carried out in an aqueous medium at room temperature. Technetium-99m labeled scintigraphic imaging agents provided according to the present invention can be prepared under reaction conditions as described in Example 2 hereinbelow.

Radioactively labeled metal chelator and metal chelator/targeting moiety conjugates are provided having a suitable amount of radioactivity for use as radiopharmaceutical agents. It is generally preferred to form radioactive complexes in solutions containing radioactivity at concentrations of from about 0.01 millicurie (mCi) to 100 mCi per mL.

The scintigraphic imaging agents which are Tc-99m-labeled metal chelator and metal chelator/targeting moiety conjugates of the invention can be used for providing images useful in diagnosing many types of disorders such as cancer, e.g. gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries. The scintigraphic imaging agents of the invention are also useful for imaging sites of infection, thrombosis, pulmonary embolism, inflammation, Alzheimer's Disease and atherosclerosis, as well as diseases of the lungs, heart, liver, kidney, bone and brain.

In accordance with this invention, Tc-99m labeled scintigraphic imaging agents are administered in a single unit injectable dose. The scintigraphic imaging agents of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma. Generally, the unit dose to be administered has a radioactivity of about 0.01 mCi to about 100 mCi, preferably 1 mCi to 20 mCi. The solution to be injected at unit dosage is from about 0.01 mL to about 10 mL. Advantageously, the dose is administered intravenously, but other routes, e.g. intraarterial, may be used. After administration, imaging of the region of interest can take place in a matter of a few minutes. However, imaging can take place, if desired, in hours or even longer, after injection into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The invention also provides radiotherapeutic agents that are Re-186, Re-188 or Sn-117m labeled metal chelators or metal chelator/targeting moiety conjugates of the invention for treating pathological conditions in a mammalian body. Tin complexes are prepared simply by reacting a metal chelator or metal chelator/targeting moiety conjugate of the invention with a radioactive stannous salt. Rhenium complexes are prepared in essentially the same way as are the technetium-99m complexes as described above and in Example 2 below. Specifically, rhenium complexes are made either by reaction of perrhenate in the presence of the chelating ligand or by reaction of pre-reduced rhenium such as oxotetrabromorhenate with the metal chelator or metal chelator/targeting moiety conjugate of the invention. For therapeutic purposes, the rhenium-186, rhenium-188, or Sn-117m complexes are provided in doses of from about 0.01 to about 100mCi, preferably from 1 to 20mCi.

The methods for making and labeling these compounds are more fully illustrated in the following Examples. These Examples illustrate certain aspects of the above-described methods and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotrile (HBTU/HOBT), and using p-hydroxymethylphenoxymethylpolystyrene (HMP) or Sasrin™ resin for carboxyl-terminus acids or Rink amide resin for carboxyl-terminus amides.

Homocysteine (Hcy) was prepared by alkaline hydrolysis of L-homocysteine lactone or by reduction of homocystine using metallic sodium in liquid ammonia. Fmoc.Hcy(S-trityl) and Fmoc.Pen(S-trityl) were prepared from the appropriate precursor amino acids by tritylation with triphenylmethanol in trifluoroacetic acid, followed by Fmoc derivitization as described by Atherton et al. (1989, *Solid Phase Peptide Synthesis*, IRL Press: Oxford). 4-piperidinyl butyl ether derivatives of tyrosine (Y[($CH_4$-piperidine]) were prepared by SPPS starting with Fmoc-tyrosine-(4-Boc-piperidine butyl ether). Fmoc-S-(3-Boc-aminopropyl)cysteine was prepared from L-cysteine and Boc-aminopropyl bromide in methanolic sodium methoxide followed by treatment with β9-fluorenylmethyl-O'-N-succcinimidyl carbonate (FmocOSu) at pH 10. 4-amidinophenylalanine (Amp) was prepared as described in co-owned and co-pending PCT International Patent Application Serial No. PCT/US94/03878, incorporated by reference.

Where appropriate, 2-haloacetyl groups were introduced either by using the appropriate 2-haloacetic acid as the last residue to be coupled during SPPS or by treating the N-terminal free amino group of the peptide bound to the resin with either 2-haloacetic acid/diisopropylcarbodiimide/N-hydroxysuccinimide in NMP or 2-halo-acetic anhydride/diisopropylethylamine in NMP.

Where appropriate, 2-haloacetylated peptides were cyclized by stirring an 0.1–1.0 mg/mL solution in phosphate or bicarbonate buffer or dilute ammonium hydroxide (pH 8) containing 0.5–1.0 mM EDTA for 4–48 hours, followed by acidification with acetic acid, iyophilization and HPLC purification.

Where appropriate, thiol-containing peptides were reacted with chloroacetyl-containing, thiol-protected Tc-99m complexing moieties at pH 10 for 0.5–4 hours at room temperature, followed by acetic acid acidification and evaporation of the solution to give the corresponding peptide-sulfide adduct. Deprotection and purification were routinely performed as described to yield the chelator-peptide conjugate.

Sasrin™ resin-bound peptides were cleaved using a solution of 1% TFA in dichloromethane to yield the protected peptide. Where appropriate, protected peptide precursors were cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products were routinely cleaved and protected sidechain-containing cyclized peptides deprotected using a solution comprised of trifluoroacetic acid (TFA), or TFA and methylene chloride, optionally also comprising water, thioanisole, ethanedithiol, and triethylsilane or triisopropylsilane in ratios of 100:5:5:2.5:2, for 0.5–3 hours at room temperature. Where appropriate, products were re-S-tritylated in triphenolmethanol/TFA, and N-Boc groups re-introduced into the peptide using (Boc)$_2$O.

Crude peptides were purified by preparative high pressure liquid chromatography (HPLC) using a Waters Delta-Pak C18 column and gradient elution with 0.1% TFA in water modified with acetonitrile. After column elution, acetonitrile was evaporated from the eluted fractions, which were then lyophilized. The identity of each product so produced and purified was confirmed by fast atom bombardment mass spectroscopy (FABMS) or electrospray mass spectroscopy (ESMS).

EXAMPLE 2

A General Method for Radiolabeling with Tc-99m

A 0.1 mg sample of a metal chelator or metal chelator/targeting moiety conjugate was dissolved in 0.1 mL of water, or 50:50 ethanol:water, or phosphate-buffered saline (PBS), or 50 mM potassium phosphate buffer (pH=5, 6 or 7.4) or 10% (w/v) hydroxypropylcyclo-dextrin (HPCD) in water. Tc-99m gluceptate was prepared by reconstituting a Glucoscan vial (E.I. DuPont de Nemours, Inc., Wilmington, Del.) with 11.0 mL of Tc-99m sodium pertechnetate containing up to 200mCi and allowed to stand for 15 minutes at room temperature. 25 μL of Tc-99m gluceptate was then added to the metal chelator or metal chelator/targeting moiety conjugate and the reaction allowed to proceed at room temperature for 5–30 min and then filtered through a 0.2 μm filter.

The radiochemical purity of the Tc-99m labeled reagent was determined by HPLC using the following conditions: a Waters Delta-Pak RP-18 analytical column, having dimensions of 5 μm×4.6 mm×220 mm, was loaded with each radiolabeled peptide, which were then eluted at a solvent flow rate of 1 mL/min. Gradient elution was performed over 10–20 min using a linear gradient beginning with 100% Solvent A (0.1% TFA/water) and ending with 100% Solution B (0.1% TFA/90% acetonitrile/water). Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

Non-radioactive rhenium complexes were prepared by co-dissolving each of the reagents of the invention with about one molar equivalent of tetrabutylammonium oxotetra-bromorhenate (+5), prepared as described by Cotton et al. (1966, *Inorg. Chem.* 5: 9–16) in dimethylformamide or acetonitrile/water and stirred for 0.5–5 days. The rhenium complexes were isolated by reverse phase HPLC as described above for Tc-99m labeled peptides and were characterized by FABMS or ESMS.

Radioactive rhenium complexes, using for example Re-186 or Re-188, are prepared from the appropriate perrhenate salts using the same protocol as for Tc-99m labeling, or by adding a reducing agent to a solution of the peptide and perrhenate, or optionally using a ligand transfer agent such as citrate and incubating the reaction at a temperature between room temperature and 100° C. for between 5 and 60 min.

The following Table illustrates successful Tc-99m labeling of peptides prepared according to Example 1 using the method described herein.

TABLE I

| Peptides | FABMS MH$^+$ | Radiochemical Yield (%)** | HPLC R$_T$ (min)*** |
|---|---|---|---|
| GGCSIPPEVKFNKPFVYLIamide | 2107 | 99[1]* | 16.5[1] |
| GGCSIPPEVKFNKPFVYLI | 2108 | 99[1] | 15.6–16.9[1] |
| GGCGLF | 553 | 96[1] | 13.7–17.1[1] |
| RGCSIPPEVKFNKPFVYLI.amide | 2207 | 95[1] | 15.2[1] |
| RGCQAPLYKKIIKKLLES | 2209 | 96[1] | 15.6[1] |
| RGCGHRPLDKKREEAPSLRPAPPPISGGYR.amide | 3355 | 97[1] | 12.4[1] |
| GGCRPKPQQFFGLM.amide | 1565 | N.D. | N.D. |
| GGCFVYLI.amide | 870 | N.D. | N.D. |
| AKCGGGF$_D$YW$_D$KTFT.amide | 1612 | 98 | 15–16[1] |
| acetyl.F$_D$FYW$_D$KTFT(ε-K)GC.amide | 1469 | 96[1] | 12.1, 12.6[2] |
| (DTPA).F$_D$FYW$_D$KTFT(ε-K)GC.amide | 1801 | 97[1] | 11.3[2] |
| K$_D$K.Nal$_D$.Cpa.YW$_D$KTFT(ε-K)GCDD.amide | 1998 | 99[1] | 14.9, 15.2[1] |
| {(CH$_2$CO.Y$_D$.Apc.GDCG)$_2$KG}$_2$.K(ε-K)GCG.amide | 3644$^E$ | N.D. | N.D. |
| {(CH$_2$CO.Y$_D$.Apc.GDCGGCG.amide)(CH$_2$CO)}$_2$.K(ε-K)GC.amide | N.D. | N.D. | |
| (CH$_2$CO.Y$_D$.Apc.GDCKKG)$_2$K(ε-K)GC.β-Ala.amide | 2267 | N.D. | N.D. |
| cyclo(N—CH$_3$)FYW$_D$KV.Hcy.(CH$_2$CO.K(ε-K)KCK.amide) | 1528 | N.D. | N.D. |
| acetyl.F$_D$FYW$_D$KTFTGGG(ε-K)GC.amide | 1640 | 98[1] | 11.9, 12.4[2] |
| (DTPA).(ε-K)GCF$_D$FYW$_D$KTFT.amide | 1802 | 97[1] | 11.5[2] |
| acetyl.F$_D$FYW$_D$KTFTGGG(ε-K)KC.amide | 1710 | 98[3] | 15.9[1] |
| F$_D$.Cpa.YW$_D$KTFTGGG(ε-K)GC.amide | 1461 | 98[2] | 15.8[1] |
| (DTPA).F$_D$.Cpa.YW$_D$KTFT(ε-K)GC.amide | 1837 | 97[2] | 15.5[1] |
| (DTPA).Nal$_D$.Cpa.YW$_D$KTFT(ε-K)GC.amide | 1887 | 97[2] | 16.2[1] |
| (DTPA).Aca.F$_D$.Cpa.YW$_D$KTFT(ε-K)GC.amide | 1950 | 97[1] | 11.5[2] |
| F$_D$.Cpa.YW$_D$K.Abu.Nal.T(ε-K)GC.amide | 1495 | 95[3] | 16.5[1] |
| CH$_2$CO.FFW$_D$KTFC(ε-K)GC.amide | 1305 | 99[3] | 16.5[1] |
| cyclo(N—CH$_3$)FYW$_D$KV.Hcy.(CH$_2$CO.K(ε-K)GC.amide) | 1328 | 97[3] | 14.5[1] |
| cyclo(N—CH$_3$)FYW$_D$KV.Hcy.(CH$_2$CO.(ε-K)GC.amide) | 1201 | 99[2] | 15.3[1] |
| (DTPA).Nal$_D$.Cpa.YW$_D$KTFT(ε-K)GCKK.amide | 2143 | 97[3] | 15.5[1] |
| K$_D$KK.Nal$_D$.Cpa.YW$_D$KTFT(ε-K)GCDDD.amide | 2241 | 98[2] | 14.9[1] |
| D$_D$DF$_D$.Cpa.YW$_D$KTFT(ε-K)GCKK.amide | 1948 | 98[2] | 14.9[1] |
| acetyl.D$_D$DF$_D$.Cpa.YW$_D$KTFT(ε-K)GCKK.amide | 1990 | 99[2] | 15.2[1] |
| K$_D$KKF$_D$K.Cpa.YW$_D$KTF.Nal.(ε-K)GCDDDD.amide | 2531 | 98[2] | 15.0[1] |
| D$_D$F$_D$.Cpa.YW$_D$KTFT(ε-K)GCKK.amide | 1832 | 99[2] | 15.0[1] |
| acetyl.KKKKK.Nal$_D$.Cpa.YW$_D$KTFT(ε-K)GC.amide | 2192 | 94[1] | 14.9[1] |

TABLE I-continued

| Peptides | FABMS MH+ | Radiochemical Yield (%)** | HPLC $R_T$ (min)*** |
|---|---|---|---|
| (DTPA).Nal$_D$.Cpa.YW$_D$KT.Nal.T($\epsilon$-K)GCKK.amide | 2192 | 95[2] | 15.8[1] |
| CH$_2$CO.FFW$_D$KTFCKKKKK($\epsilon$-K)GC.amide | 1947 | 99[3] | 15.8[1] |
| CH$_2$CO.FFW$_D$KTFC($\epsilon$-K)KKKKKGC.amide | 1947 | 99[2] | 14.9[1] |
| DDDD.Nal$_D$.Cpa.YW$_D$KTFT($\epsilon$-K)GCKKKK.amide | 2484 | 99[3] | 15.1[1] |
| Nal$_D$.Cpa.YW$_D$KTFT($\epsilon$-K)GCKK.amide | 1767 | 98[3] | 15.8[1] |
| (2-ketogulonyl).F$_D$.Cpa.YW$_D$KTFT($\epsilon$-K)GC.amide | 1638 | 99[1] | 15.8, 16.1[1] |
| KDKD.NalD.Cpa.YW$_D$KTFT($\epsilon$-K)GCKDKD.amide | 2484 | 99[3] | 14.8[1] |
| acetyl.KKKKK.Nal$_D$.Cpa.YW$_D$KTFT($\epsilon$-K)GCKK.amide | 2450 | 99[3] | 14.2[1] |
| KKKK.Nal$_D$.Cpa.YW$_D$KTFT($\epsilon$-K)GCDDDD.amide | 2485 | 99[3] | 14.6[1] |
| (2-ketogulonyl).Nal$_D$.Cpa.YW$_D$KTFT($\epsilon$-K)GCKK.amide | N.D. | 99[3] | 16.0[1] |
| Trc.Nal$_D$.Cpa.YW$_D$KTFT($\epsilon$-K)GCKK.amide | 1926 | 99[3] | 16.3[1] |
| acetyl.D$_D$F$_D$.Cpa.YW$_D$KTFT($\epsilon$-K)GCKK.amide | 1875 | 99[2] | 15.4[1] |
| F$_D$.Cpa.YW$_D$KTFT($\epsilon$-K)GCKK.amide | 1717 | 99[2] | 15.0[1] |
| Nal$_D$.Cpa.YW$_D$KTFT($\epsilon$-K)GCKK.amide | 1768 | 97[2] | 15.8[1] |
| F$_D$FYW$_D$KTFT($\epsilon$-K)GCKK.amide | 1683 | 98[2] | 14.5[1] |
| (CH$_2$CO.Y$_D$.Apc.GDC)$_2$K.($\epsilon$-K)GCG.amide | 1768$^E$ | 96[1] | 12.1[1] |
| Hca.Nal$_D$.Cpa.YW$_D$KTFT($\epsilon$-K)GCKK.amide | 2097 | 99[3] | 15.8[1] |
| (Trc)$_2$.Nal$_D$.Cpa.YW$_D$KTFT($\epsilon$-K)GCKK.amide | 2212 | 99[3] | 15.6[1] |
| K$_D$KKK.Nal$_D$.Cpa.YW$_D$KTFT($\epsilon$-K)GCDD.amide | 2253 | 98[3] | 14.7[1] |
| K$_D$DKD.Nal$_D$.Cpa.YW$_D$KTFT($\epsilon$-K)GCKDKD.amide | 2485 | 99[3] | 14.8[1] |
| cyclo(N—CH$_3$)FYW$_D$KV.Hcy.(CH$_2$CO.KKKKK($\epsilon$-K)GC.amide) | 1841 | 98[2] | 13.4[1] |
| acetyl.KK($\epsilon$-K)GCGCGGPLYKKIIKKLLES | 2275 | 98[1]* | 15.1[1] |
| F$_D$.Cpa.YW$_D$KTFT($\epsilon$-K)GCR.amide | 1617 | 99[3] | 15.4[1] |
| (Trc-imide).Nal$_D$.Cpa.YW$_D$KTFT($\epsilon$-K)GCR.amide | 1808 | 99[3] | 15.4[1] |
| Trc.(Trc-imide).K.Nal$_D$.Cpa.YW$_D$KTFT($\epsilon$-K)GCRR.amide | 2250 | 100[3] | 16.7[1] |
| (Trc-imide)$_2$.Nal$_D$.Cpa.YW$_D$KTFT($\epsilon$-K)GCR.amide | 2232 | 99[3] | 16.6[1] |
| cyclo(N—CH$_3$)FYW$_D$KV.Hcy.(CH$_2$CO.($\epsilon$-K)GCK.amide) | 1329 | 99[3] | 14.7[1] |
| (acetyl.TKPRGG)$_2$($\epsilon$-K)GC.amide | 1710 | 97[1] | 11.1, 11.4[1] |
| ({CH$_2$CO.Y$_D$.Apc.GDCGGC$_{Acm}$GC$_{Acm}$GGC.amide)(CH$_2$CO)}$_2$.K)$_2$K-($\epsilon$-K)GCG.amide | 6478$^E$ | N.D. | N.D. |
| (CH$_2$CO.Y$_D$.Apc.GDCGGC$_{Acm}$GC$_{Acm}$GGC.amide)$_2$(CH$_2$CO)$_2$K,($\epsilon$-K)GC.amide | 3298$^E$ | N.D. | N.D. |
| K$_D$.Nal$_D$.Cpa.YW$_D$KTFT($\epsilon$-K)GCD.amide | 1755 | 99[1] | 15.5[1] |
| acetyl-DDD.Nal$_D$.Cpa.YW$_D$KTFT($\epsilon$-K)GCKK.amide | 2040 | 100[2] | 16.0 |
| (CH$_2$CO.Y$_D$.Amp.GDC.GGC$_{Acm}$GC$_{Acm}$GGC.amide)$_2$(CH$_2$CO)$_2$K($\epsilon$-K)GC.amide | 3378$^E$ | 98[4] | 4.6[3] |
| (CH$_2$CO.Y$_D$.Amp.GDC.KGCG.amide)$_2$(CH$_2$CO)$_2$K($\epsilon$-K)GC.amide | 2573$^E$ | 99[4] | 44[3] |
| acetyl-KKKKKK($\epsilon$-K)GCGGPLYKKIIKKLLES | 2658 | 98[4] | 6.1[3] |
| cyclo(N—CH$_3$)FYW$_D$KV.Hcy.(CH$_2$CO.($\beta$-Dap)GCK.amide) | 1287$^E$ | N.D. | N.D. |
| cyclo(N—CH$_3$)FYW$_D$KV.Hcy.(CH$_2$CO.($\delta$-Orn)GCK.amide) | 1315$^E$ | N.D. | N.D. |
| cyclo(N—CH$_3$)FYW$_D$KV.Hcy.(CH$_2$CO.($\gamma$-Dab)KCR.amide) | 1400 | N.D. | N.D. |
| cyclo(N—CH$_3$)FYW$_D$KV.Hcy.(CH$_2$CO.($\beta$-Dap)KCK.amide) | 1358 | 97[4] | 7.0[3] |
| cyclo(N—CH$_3$)FYW$_D$KV.Hcy.(CH$_2$CO.($\beta$-Dap)KCR.amide) | 1386 | 98[4] | 7.0[3] |
| cyclo(N—CH$_3$)FYW$_D$KV.Hcy.(CH$_2$CO.GC.Dap.Dap.amide) | 1245 | 77[4] | 7.8[3] |

**Superscripts refer to the following labeling conditions:
[1]=in water
[2]=in 10% HPCD
[3]=in 50/50 ethanol/water
[4]=in 0.9% NaCl
[5]=in water made pH 9 with NaHCO$_3$
***HPLC methods (indicated by superscript after $R_T$):
Solvent A=0.1% TFA in water
Solvent B 0.1% TFA/CH$_3$CN in water
Waters-1 column=Waters DeltaPak C18, 5 μm, 39 mm×150 mm (flow rate: 1.2 mL/min)
Waters-2 column=Waters NovaPak Radial Compression C18, 4 μm, 8 mm×100 mm (flow rate: 3 mL/min)
Vydac column=Vydac 218TP54 RP-18, 5 μm, 4.6 mm×220 mm (flow rate: 1 mL/min)
Method 1=Waters-1 column, 100% Solution A→100% Solution B in 10 min
Method 2=Vydac column, 100% Solution A→100% Solution B in 10 min
Method 3=Waters-2 column, 100% Solution A→100% Solution B in 10 min
Single-letter abbreviations for amino acids can be found in G. Zubay, *Biochemistry* (2d. ed.), 1988 (MacMillen Publishing: New York) p. 33. Underlining indicates the formation of an amide or a thiol linkage between the linked amino acids or derivative groups. Acm is acetamidomethyl; Orn is ornithine; F$_D$ is D-phenylalanine; Y$_D$ is D-tyrosine; W$_D$ is D-tryptophan; K$_D$ is D-lysine; D$_D$ is D-aspartate; Apc is L-(S-(3-aminopropyl)cysteine); Hcy is homocysteine; Nal is 2-naphthylalanine; Nal$_D$ is D-2-naphthylalanine; DPTA is diethylenetriaminepentaacetic acid; Cpa is 4-chlorophenylalanine; Aca is 6-aminohexanoic acid; Abu is aminoisobutyric acid; Trc is tricarballylic acid; Trc-imide is tricarballylic imide; and Hca is hexacarboxycyclohexane. ( . . . )$_2$K represents covalent linkage to both amino groups of lysine. Hcy( . . . ) represents covalent linkage to the sidechain sulfur atom of homocysteine. (N—CH$_3$)F represents N-α-methylphenylalanine. Underlining between groups (e.g., as between the CH$_2$CO. group and cysteine (C) in CH$_2$CO.Y$_D$RGDC) represents a cyclic sulfide. Underlining between amino acids (e.g., as between the cysteines (C) in CNPRGDC) represents a cyclic disulfide bond. The term "cyclo" before an underlined sequence means an N-terminus-to-C-terminus cyclic sequence. The subscript X$_D$ indicates the amino acid is in the D-configuration; all other subscripts refer to amino acid sidechain protecting groups.

EXAMPLE 3

Platelet Aggregation Inhibition Assays

Platelet aggregation studies were performed essentially as described by Zucker (1989, *Methods in Enzymol.* 169: 117–133). Briefly, platelet aggregation was assayed with or without putative platelet aggregation inhibitory compounds using fresh human platelet-rich plasma, comprising 300,000 platelets per microlitre. Platelet aggregation was induced by the addition of a solution of adenosine diphosphate to a final concentration of 10 to 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 μg/mL. The concentration of inhibitor that reduced the extent of platelet aggregation by 50% (defined as the $IC_{50}$) was determined from plots of inhibitor concentration versus extent of platelet aggregation. An inhibition curve for peptide RGDS was determined for each batch of platelets tested as a positive control.

The following peptide reagents were tested in the above assay:

P688={($CH_2CO.Y_D$.Apc. $GDCGGC_{Acm}GC_{Acm}GGC_{amide}$)$_2$ ($CH_2CO)_2K$}$_2$.K(ε-K)GCG.amide P748=($CH_2CO.Y_D$.Apc.GDCKGCG.amide)$_2$($CH_2CO)_2$K(ε-K)GC.amide P747=($CH_2CO.Y_D$.Amp.$GDCGGC_{Acm}GC_{Acm}GGC$.amide)$_2$ ($CH_2CO)_2$K(ε-K)GC.amide P687=($CH_2CO.Y_D$.Apc.GDCKGG)$_2$K(ε-K)GC.β-Ala.amide P681={($CH_2CO.Y_D$Apc.GDCG)$_2$KG}$_2$K(ε-K)GCG.amide P667=($CH_2CO.Y_D$.Apc.$GDCGGC_{Acm}GC_{Acm}GGC$.amide)$_2$ ($CH_2CO)_2$K(ε-K)GC.amide The results of these experiments are shown in Table II (RGDS is given as a positive control):

TABLE II

| Peptide | $IC_{50}$* |
| --- | --- |
| P688 | 0.026 |
| P748 | 0.029 |
| P747 | 0.052 |
| P687 | 0.079 |
| P681 | 0.110 |
| P667 | 0.110 |

* = μM (Single-letter abbreviations for amino acids can be found in G. Zubay, *Biochemistry* (2d. ed.), 1988 (MacMillen Publishing: New York) p. 33 as discussed in the Legend of Table I.

These results demonstrate that peptide reagents of the invention bind with high affinity to specific GPIIb/IIIa receptors in vitro.

EXAMPLE 4

In Vivo Imaging of Deep Vein Thrombosis using a Tc-99m Labeled Thrombus Targeting Peptide in a Canine Model Mongrel dogs (25–35 lb., fasted overnight) were sedated with a combination of ketamine and aceprozamine intramuscularly and then anesthetized with sodium pentabarbital intravenously. In each animal, an 18-gauge angiocath was inserted in the distal half of the right femoral vein and a 5 mm or 8 mm Dacron®-entwined stainless steel embolization coil (Cook Co., Bloomington Ind.) was placed in the femoral vein at approximately mid-femur. The catheter was removed, the wound sutured and the placement of the coil documented by X-ray. The animals were then allowed to recover overnight.

One day following coil placement, each animal was re-anesthetized, intravenous saline drips placed in each foreleg and a urinary bladder catheter inserted to collect urine. The animal was placed supine under a gamma camera equipped with a low-energy, all purpose collimator and photopeaked for Tc-99m. Tc-99m labeled thrombus targeting peptides [185–370 mBq (5–10 mCi) Tc-99m, 0.2–0.4 mg reagent] were each injected into one foreleg intravenous line at its point of insertion. The second line was maintained for blood collection.

Gamma camera imaging was started simultaneously with injection. Anterior images over the heart were acquired as a dynamic study (10 sec image acquisitions) over the first 10 min, and then as static images at 1, 2, 3 and 4h post-injection. Anterior images over the legs were acquired for 500,000 counts or 20 min (whichever is shorter), at approximately 10–20 min, and at approximately 1, 2, 3 and 4h post-injection. Leg images were collected with a lead shield placed over the bladder.

Following collection of the final image, each animal was deeply anesthetized with pentobarbital. Two blood samples were collected using a heparinized syringe followed by a euthanizing dose of saturated potassium chloride solution administered by intercardiac or bolus intravenous injection. The femoral vein containing the thrombus, a similar section of vein of the contralateral (control) leg, sections of the vessel proximal to the thrombus and samples of thigh muscle were then carefully dissected out. The thrombus, coil and coil Dacron fibres were then dissected free of the vessel. The thrombus, saline-washed vessel samples, coil and coil Dacron® fibres were separated, and each sample was placed in a pre-weighed test tube. The samples were weighed and counted in a gamma well counter in the Tc-99m channel, along with known fractions of the injected doses.

Fresh thrombus weight, percent injected dose (% ID)/g in the thrombus and blood obtained just prior to euthanasia and thrombus/blood and thrombus/muscle ratios were determined. From the computer-stored images, thrombus/background ratios were determined by analysis of the counts/pixel measured in regions-of-interest (ROI) drawn over the thrombus and adjacent muscle.

Representative results are shown in Table III. Peptides are identified by number, corresponding to the chemical structure shown in Table II. These results show that each of these representative peptides are usefulo as efficient scitigraphic imaging agents in vivo when Tc-99m labeled, administered and imaged as described herein.

TABLE III

| Peptide | % ID/g Thrombus | Thrombus/Blood | Thrombus/Muscle |
| --- | --- | --- | --- |
| P748 | 0.034 | 5.8 | 90 |
| P747 | 0.043 | 15 | 70 |
| P667 | 0.006 | 5.9 | 30 |

EXAMPLE 5

Localization and In Vivo Imaging of Atherosclerotic Plaque Using Tc-99m Labeled Scintigraphic Imaging Agents in a Hypercholesterol Rabbit Model New Zealand White (NZW) rabbits of both sexes and weighing 2–3 kg are divided into two groups. The control group consists of 6 rabbits that are housed and fed commercial rabbit chow (Purina). The HC group is fed a standardized, cholesterol-rich diet (rabbit chow mixed to a 1% w/w concentration of cholesterol) from seven weeks until 28 weeks of age. All animals are given water ad libitum.

Tc-99m labeled atherosclerotic plaque imaging agents are prepared as described above. Approximately 1000 μg of peptide is labeled with 100–200mCi of Tc-99m and prepared in unit doses of 5–10mCi (12.5–20.0 μg/rabbit; 6–7 μg/kg) in 0.5–2 mL volume. Adult rabbits are dosed with each of the Tc-99m labeled imaging agents intravenously in a lateral ear vein by slow bolus infusion (approximately 0.1 mL/min). Scintiphotos are acquired using a gamma camera fitted with a pin-hole collimator (5 mm aperture) and energy window set for Tc-99m and programmed to accumulate 500,000 counts or scan for a desired time. Shortly before imaging, animals are anesthetized with a mixture of ketamine and xylazine (5:1, 1 mL/kg intramuscularly).

Gamma camera images are collected at 40°–45° just above the heart (left anterior oblique [LAO] view) to delineate the aortic arch and view the descending aorta. Images are acquired at 15 min and 2h after injection. Supplementary anesthesia is injected as needed prior to each image collection.

At 2.5 h (after a 2 h scan), animals are sacrificed with an intravenous dose of sodium pentobarbital. Upon necropsy, the aorta is removed and branching vessels dissected free from the aortic valve to the mid-abdominal region. Using a parallel hole collimator, the aorta is imaged ex corpora. As a control, the aortae are opened longitudinally and stained with Sudan IV, thereby turning atherosclerotic plaque a deep red brick color. Lipid-free and uninjured aortic endothelium, in contrast, retains its normal, glistening white-pink appearance under these conditions. Thus, this protocol can be used to unambiguously confirm the presence of atherosclerotic plaque detected using the scintigraphic imaging agents of the invention.

EXAMPLE 6

Scintigraphic Imaging and Biodistribution of Tc-99m Infection Targeting Agents in an Animal Model of Infection New Zealand White (NZW) rabbits of both sexes and weighing 2–3 kg were innoculated intramuscularly in the left calf with a potent strain of *Escherichia coli*. After 24 hours, the animals were sedated by intramuscular injection of ketamine and xylazine and then injected with Tc-99m labeled infection targeting agent (2–10mCi, <150 μg). The animals were then positioned supine in the field of view of a gamma cammera (LEAP collimator/photopeaked for Tc-99m) to be imaged. The animals were imaged over the first hour post-injection, and then at approximately 1 hour intervals for the next 3 hours. Animals were allowed to recover between image acquisiitons and re-anesthetized as needed.

Upon completion of the final imaging, each animal was sacrificed with an intravenous overdose of sodium pentobarbital, then dissected to obtain samples of blood and of infected and control tissue. Tissue samples were weighed and counted using a gamma radition counter; a standard amount the injected dose was counted in parallel with each sample as a control. From these data the percent of the injected dose per gram of tissue remaining in each tissue sample was determined. Ratios of percent of injected dose per gram of infected tissue versus non-infected muscle tissue, and of infected muscle tissue versus blood, were then calculated for each peptide to demonstrate specific localization of radiolabeled scintigraphic imaging agents of the invention.

Results of these experiments are shown in Table IV. These results show that these representative agents are useful as scintigraphic imaging agents for detecting sites of inflammation in a mammalian body.

TABLE IV

| Peptides | Infected Muscle (% ID/g) | Control Muscle (% ID/g) | Ratio of Infected/ Control | Blood (% ID/g) | Ratio of Infected/ Blood |
|---|---|---|---|---|---|
| GGCSIPPEVKFNKPFVYLI.amide (P472) | 0.0079 | 0.0009 | 8.8 | 0.0076 | 1.0 |
| GGCGLF (P477) | 0.0100 | 0.0012 | 8.4 | 0.0140 | 0.72 |

(% ID/g) = percent injected dose per gram tissue; other abbreviations are as in the previous Tables.

EXAMPLE 7

Inhibition of [$^{125}$I-Tyr$^{11}$]Somatostatin-14 Binding to AR42J Rat Pancreatic Tumor Cell Membranes The ability of various somatostatin analogues of the invention to bind to somatostatin receptors in vitro was demonstrated in an assay of peptide reagent-mediated inhibition of binding of a radiolabeled somatostatin analogue to somatostatin receptor-containing cell membranes.

The rat pancreatic tumor cell line AR42J expressing the somatostatin receptor was cultured in Dulbecco's modified essential media (DMEM) supplemented with 10% fetal calf serum (FCS) and 8 mM glutamine in a humidified 5% $CO_2$ atmosphere at 37° C. Harvested cells were homogenized in cold buffer (50 mM Tris-HCl, pH 7.4), and the homogenate was then centrifuged at 39,000 g for 10 min at 4° C. Pellets were washed once with buffer and then resuspended in ice-cold 10 mM Tris-HCl buffer (pH 7.4). Equal aliquots of this cell membrane preparation were then incubated with [$^{125}$I-Tyr$^{11}$]somatostatin-14 (Amersham, Arlington Heights, Ill.) at a final concentration of 0.5 nM at 750,000 cpm/mL, specific activity 2000Ci/mmol and either a peptide or peptide-rhenium complex of the invention (at a final concentration ranging from $10^{-11}$ to $10^{-6}$ in 50 mM HEPES buffer, pH 7.4, containing 1% bovine serum albumin, 5 mM $MgCl_2$, 0.02 mg/mL bacitracin, 0.02 mg/mL phenylmethyl-sulfonylfluoride and 200,000 IU Trasylol) for 25 min at 30° C.

After incubation, this membrane mixture was filtered through a polyethyleneimine-washed GC/F filter (Whatman Ltd., Maidstone, England) using a filtration manifold, and the residue remaining on the filter was washed three times with 5 mL cold HEPES buffer. The filter and a sample of the filter washings were then counted on a gamma counter. To assess non-specific binding, the assay was also performed essentially as described in the presence of 200 mg unlabeled somatostatin-14. Data analysis included Hill plots of the data to yield inhibition constants as described by Bylund and Yamamura (1990, Methods in Neurotransmitter Receptor Analysis, Yamamura et al., eds., Raven Press: N.Y.).

The following peptides were tested:
P487=cyclo(N—$CH_3$)FYW$_D$KV.Hcy.($CH_2CO$).K($\epsilon$-K)GC.amide
P498=(DTPA).Nal$_D$.Cpa.YW$_D$KTFT($\epsilon$-K)GCKK.amide
P398=AKCGGGF$_D$YW$_D$KTFT.amide
P524=(DTPA).Nal$_D$.Cpa.YW$_D$KT.Nal.T($\epsilon$-K)GCKK.amide
P468=cyclo(N-$CH_3$)FYW$_D$KV.Hcy.($CH_2CO$).($\epsilon$-K)GC.amide
P545=KDKD.Nal$_D$.Cpa. YWDKTFT($\epsilon$-K)GCKDKD.amide
P544=(2-ketogulonyl)F$_D$.Cpa.YW$_D$KTFT($\epsilon$-K)GC.amide
P548=acetyl.Nal$_D$.Cpa.YW$_D$KTFT($\epsilon$-K)GCKK.amide
P591=cyclo(N-$CH_3$)FYW$_D$KV.Hcy.($CH_2CO$).($\epsilon$-K)GCK.amide The results obtained using this assay with the reagents of the invention are as follows:

TABLE V

| Peptides | $K_i$(nM) |
|---|---|
| P487 | 0.65 |
| P498 | 1.3 |
| P398 | 1.4 |
| P524 | 2.0 |
| P468 | 2.0 |
| P545 | 2.6 |
| P544 | 2.7 |
| P548 | 3.6 |
| P591 | 4.2 |

These results demonstrate that peptide reagents of the invention bind with high affinity to somatostatin receptors in vitro.

EXAMPLE 8

Localization and In Vivo Imaging of Somatostatin Receptor (SSTR)-Expressing Tumors in Rats In vivo imaging of somatostatin receptors expressed by rat tumor cells was performed essentially as described by Bakker et al. (1991, Life Sciences 49: 1593–1601).

CA20948 rat pancreatic tumor cells, thawed from frozen harvested tumor brei, were implanted intramuscularly into the right hind thigh of 6 week old Lewis rats in a suspension of 0.05 to 0.1 mL/animal. The tumors were allowed to grow to approximately 0.5 to 2 g, harvested, and tumor brei was used to implant a second, naive set of Lewis rats. Passaging in this fashion was repeated to generate successive generations of tumor-bearing animals. The tumor-bearing animals used for the in vivo studies were usually from the third to fifth passage and carried 0.2 to 2 g tumors.

For studies of the specificity of radiotracer localization in the tumors, selected animals were given an subcutaneous SSTR-blocking dose (4 mg/kg) of octreotide 30 minutes prior to injection of the radiotracer. (This protocol has been shown by Bakker et al. to result in a lowering of $^{111}$In-[DTPA]octreotide tumor uptake by 40%.)

Third- to fifth-passage CA20948 tumor-bearing Lewis rats were restrained and injected intravenously via the dorsal tail vein with a dose of 0.15–0.20 mCi of a $^{99m}$Tc-labeled SSTR targeting imaging agent of the invention (corresponding to 3 to 8 μg peptide in 0.2 to 0.4 mL).

At selected times, the animals were sacrificed by cervical dislocation and selected necropsy was performed. Harvested tissue samples were weighed and counted along with an aliquot of the injected dose in a gamma well-counter.

The 90-minute biodistribution results of selected radiolabeled peptides are presented in Table VI. Notably, $^{99m}$Tc-P832, $^{99m}$Tc-P829, and $^{99m}$Tc-P773 showed very high tumor uptake and tumor/blood ratios demonstrating their high specific uptake in target (tumor) tissue. These results demonstrate that representative scintigraphic imaging agents of the invention can be used to localize the site of somatostatin receptor-expressing neoplastic cells in vivo, and thus have efficacy as cancer radiodiagnostic and radiotherapeutic agents It should be understood that the foregoing disclosure emphasizes certain specific embodiments of the invention and that all modifications or alternatives equivalent thereto are within the spirit and scope of the invention as set forth in the appended claims.

TABLE VI

| No. | Peptides | % ID/g | | |
|---|---|---|---|---|
| | | Tumor | Blood | Tumor/Blood |
| P832 | cyclo(N-methyl)FYW$_D$KV.Hcy.($CH_2$CO.(β-Dap)KCR.amide) | 2.7 | 0.20 | 13 |
| P829 | cyclo(N-methyl)FYW$_D$KV.Hcy.($CH_2$CO.(β-Dap)KCK.amide) | 2.7 | 0.20 | 13 |
| P773 | cyclo(N-methyl)FYW$_D$KV.Hcy.($CH_2$CO.(δ-Orn)GCK.amide) | 1.9 | 0.13 | 15 |
| P772 | cyclo(N-methyl)FYW$_D$KV.Hcy.($CH_2$CO.(δ-Dap)GCK.amide) | 1.5 | 0.24 | 7.2 |
| P723 | cyclo(N-methyl)FYW$_D$KV.Hcy.($CH_2$CO.($\epsilon$-K)GCKK.amide) | 1.4 | 0.26 | 5.4 |

What is claimed is:

1. A reagent comprising a targeting moiety covalently linked via a bivalent linking group to a metal chelator in which the metal chelator and the bivalent linking group together have the formula:

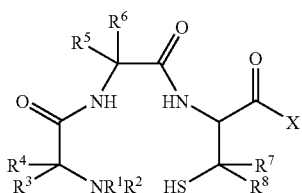

wherein:

$R^1$ and $R^2$ are each independently H, lower alkyl, hydroxyalkyl ($C_2$–$C_4$), or alkoxyalkyl ($C_2$–$C_4$);

$R^3$, $R^4$, $R^5$, and $R^6$ are independently H, substituted or unsubstituted lower alkyl or phenyl not comprising a thiol group, and one of $R^3$, $R^4$, $R^5$, and $R^6$ is —L—$(CR_2)_n$- where n is an integer from 1 to 6, and each R is independently H, lower alkyl, or substituted lower alkyl;

$R^7$ and $R^8$ are each independently H, lower alkyl, lower hydroxyalkyl or lower alkoxyalkyl;

X is —$NH_2$, —$NR^1R^2$, or —$NR^1$-Y, where Y is an amino acid, an amino acid amide, or a peptide of from 2 to about 20 amino acids; and L is the bivalent linking group.

2. A reagent according to claim 1, wherein the metal chelator and the bivalent linking group together have the formula:

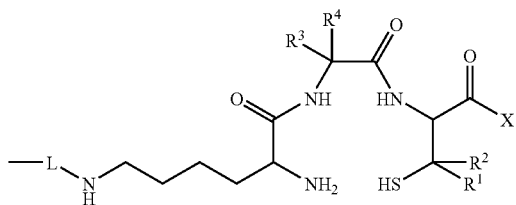

wherein:

R¹ and R² are each independently H, lower alkyl, hydroxyalkyl ($C_2$–$C_4$) or alkoxyalkyl ($C_2$–$C_4$);

R³ and R⁴ are independently H, substituted or unsubstituted lower alkyl or phenyl not comprising a thiol group;

X is —$NH_2$, —$NR^1R^2$, or —$NR^1$-Y, where Y is an amino acid, an amino acid amide, or a peptide of from 2 to about 20 amino acids; and L is the bivalent linking group.

3. A reagent according to claim 2, wherein the metal chelator and the bivalent linking group together have the formula:

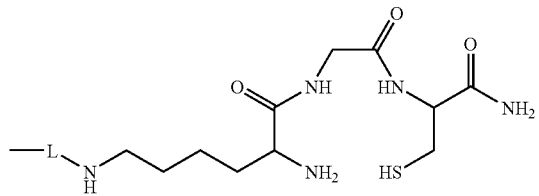

wherein:

L is bivalent linking group.

4. A reagent according to claim 1, wherein the metal chelator is selected from the group consisting of (amino acid)¹-(amino acid)²-cysteine- and (amino acid)¹-(amino acid)²-penicillaminewherein:

(amino acid)¹ does not comprise a thiol and is either an α,ω- or a β,ω-diamino acid having a free α-amine or β-amine, and (amino acid)² is a primary α- or β-amino acid not comprising a thiol.

5. A reagent according to claim 4, wherein the metal chelator has a formula selected from the group consisting of:

-(ε-Lys)-Gly-Cys-,
-(δ-Orn)-Gly-Cys-,
-(γ-Dab)-Gly-Cys- and
-(β-Dap)-Gly-Cys-.

* * * * *